(12) United States Patent
Blasco et al.

(10) Patent No.: US 7,307,172 B2
(45) Date of Patent: Dec. 11, 2007

(54) 7-AMINO TRIAZOLOPYRIMIDINES FOR CONTROLLING HARMFUL FUNGI

(75) Inventors: Jordi Tormo i Blasco, Limburgerhof (DE); Hubert Sauter, Mannheim (DE); Bernd Müller, Frankenthal (DE); Markus Gewehr, Kastellaun (DE); Wassilios Grammenos, Ludwigshafen (DE); Thomas Grote, Wachenheim (DE); Andreas Gypser, Mannheim (DE); Joachim Rheinheimer, Ludwigshafen (DE); Ingo Rose, Mannheim (DE); Peter Schäfer, Ottersheim (DE); Frank Schieweck, Hessheim (DE); Eberhard Ammermann, Heppenheim (DE); Siegfried Strathmann, Limburgerhof (DE); Gisela Lorenz, Hambach (DE); Reinhard Stierl, Mutterstadt (DE); Günter Krummel, Vendersheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 374 days.

(21) Appl. No.: 10/484,250

(22) PCT Filed: Jul. 16, 2002

(86) PCT No.: PCT/EP02/07893

§ 371 (c)(1),
(2), (4) Date: Jan. 20, 2004

(87) PCT Pub. No.: WO03/009687

PCT Pub. Date: Feb. 6, 2003

(65) Prior Publication Data

US 2005/0261314 A1    Nov. 24, 2005

(30) Foreign Application Priority Data

Jul. 26, 2001 (DE) .............................. 101 36 118

(51) Int. Cl.
*A61K 31/41* (2006.01)
*A01N 43/653* (2006.01)
*C07D 249/00* (2006.01)

(52) U.S. Cl. ............... 548/262.4; 514/383; 548/262.2; 548/262.8; 548/269.2; 504/272

(58) Field of Classification Search ............. 548/262.2, 548/262.4, 268.8, 269.2; 514/383; 504/272
See application file for complete search history.

(56) References Cited

U.S. PATENT DOCUMENTS

| 4,617,303 A | 10/1986 | Eicken et al. |
| 5,231,094 A | 7/1993 | Bru-Magniez et al. |
| 5,387,747 A | 2/1995 | Bru-Magniez et al. |
| 5,612,345 A * | 3/1997 | Becher et al. ......... 514/259.31 |

FOREIGN PATENT DOCUMENTS

| EP | 550 113 | 7/1993 |
| EP | 6139000 | * 3/1994 |
| EP | 613 900 | 9/1994 |
| EP | 770 615 | 5/1997 |
| WO | 94/20501 | 9/1994 |
| WO | 98/46608 | 10/1998 |

OTHER PUBLICATIONS

Heterocycles, vol. 43, No. 5, 1996, Shiotani et al. 1031-1047.
Tetrahedron Letters No. 24, 2661-2668, 1996, Yoffe et al. Apr. 1996.

* cited by examiner

*Primary Examiner*—Bruck Kifle
*Assistant Examiner*—Paul V. Ward
(74) *Attorney, Agent, or Firm*—Novak Druce & Quigg LLP

(57) ABSTRACT

The invention relates to 7-amino triazolopyrimidines of formula (I), in which the substituents have the following meanings: $R^1$, $R^2$ represent hydrogen, alkyl, alkenyl, alkynyl, cycloalkyl, phenyl, naphthyl; or 5-membered or 6-membered heterocyclyl containing one to four nitrogen atoms or one to three nitrogen atoms and one sulfur or oxygen atom; or 5-membered or 6-membered heteroaryl containing one to four nitrogen atoms or one to three nitrogen atoms and one sulfur or oxygen atom, or $R^1$ and $R^2$ can, together with the nitrogen atom, which binds them, form a 5-membered or 6-membered ring containing one to four nitrogen atoms or one to three nitrogen atoms and one sulfur or oxygen atom; $R^3$ represents alkyl, alkenyl, alkynyl, cycloalkyl, phenylalkyl and alkyl halide; whereby $R^3$ and $R^2$ can be unsubstituted or partially or completely substituted according to the description; X represents halogen, cyano, alkoxy, alkyl halide, phenyl or phenyl that is substituted by $R^a$. The invention also relates to methods and intermediate products for producing said compounds, to agents containing the same, and to their use.

10 Claims, No Drawings

7-AMINO TRIAZOLOPYRIMIDINES FOR CONTROLLING HARMFUL FUNGI

The present invention relates to 7-aminotriazolopyrimidines of the formula I, $$\text{I}$$

where:
$R^1$, $R^2$ are hydrogen, $C_1$-$C_{10}$-alkyl, $C_2$-$C_{10}$-alkenyl, $C_2$-$C_{10}$-alkynyl, $C_3$-$C_8$-cycloalkyl, phenyl, naphthyl; or
  5- or 6-membered heterocyclyl containing one to four nitrogen atoms or one to three nitrogen atoms and one sulfur or oxygen atom; or
  5- or 6-membered heteroaryl containing one to four nitrogen atoms or one to three nitrogen atoms and one sulfur or oxygen atom,
  where $R^1$ and $R^2$, independently of one another, may, if they are not hydrogen, be partially or fully halogenated and/or may carry one to three radicals from the group $R^a$
$R^a$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylamino, di-$C_1$-$C_6$-alkylamino, $C_2$-$C_6$-alkenyl, $C_2$-$C_6$-alkenyloxy, $C_2$-$C_6$-alkynyl, $C_3$-$C_6$-alkynyloxy and unhalogenated or halogenated oxy-$C_1$-$C_4$-alkyleneoxy,
  or
  $R^1$ and $R^2$ together with the linking nitrogen atom may form a 5- or 6-membered ring which contains one to four nitrogen atoms or one to three nitrogen atoms and one sulfur or oxygen atom and which may be substituted by one to three radicals from the group $R^a$;
$R^3$ is $C_1$-$C_{10}$-alkyl, $C_2$-$C_{10}$-alkenyl, $C_2$-$C_{10}$-alkynyl-, $C_3$-$C_8$-cycloalkyl, phenyl-$C_1$-$C_{10}$-alkyl,
  where $R^3$ may be unsubstituted or partially or fully halogenated and/or may carry one to three radicals from the group $R^a$, or
  $C_1$-$C_{10}$-haloalkyl which may carry one to three radicals from the group $R^a$;
X is halogen, cyano, $C_1$-$C_4$-alkoxy, $C_1$-$C_4$-haloalkyl, phenyl or $R^a$-substituted phenyl;

and their salts.

Additionally, the invention relates to processes and intermediates for preparing the compounds I, and also to compositions and to the use of the compounds I for controlling harmful fungi.

6-Aryltriazolopyrimidines are disclosed in WO 98/46608 and EP-A 550 113. 6-Benzyltriazolopyrimidines which are specifically substituted by aromatic groups and have pharmaceutical action are known from U.S. Pat. No. 5,231,094 and U.S. Pat. No. 5,387,747. EP-A 141 317 discloses 7-aminotriazolopyrimidines which may carry an alkyl radical in the 5-position. 6-cycloalkyltriazolopyrimidines having various radicals in the 5-position are mentioned in EP-A 613 900.

The compounds described in WO 98/46608, EP-A 550 113, EP-A 141 317 and EP-A 613 900 are suitable for use as crop protection agents against harmful fungi.

However, in many cases their action is unsatisfactory. It is an object of the present invention to provide compounds having improved activity.

We have found that this object is achieved by the 7-aminotriazolopyrimidines of the formula I. Furthermore, we have found intermediates and processes for preparing the compounds I, and the use of the compounds I and of compositions comprising them for controlling harmful fungi.

The compounds of the formula I differ from the compounds known from the abovementioned publications by the combination of the substituents X with the radical $R^3$ on the triazolopyrimidine skeleton.

Compounds of the formula I in which X is halogen are obtained, for example, from dicarbonyl compounds of the formula II.1, which are cyclized with 3-amino-1,2,4-triazole of the formula III to give hydroxytriazolopyrimidines of the formula IV.1:

This reaction is usually carried out at temperatures of from 25° C. to 210° C., preferably from 120° C. to 180° C., in the presence of a base [cf. EP-A-770615].

Suitable bases are, in general, organic bases, for example tertiary amines, such as trimethylamine, triethylamine, triisopropylethylamine, tributylamine and N-methylpiperidine and pyridine. Particular preference is given to triethylamine and tributylamine.

The bases are generally employed in catalytic amounts; however, they can also be employed in equimolar amounts, in excess or, if appropriate, as solvent.

The starting materials are generally reacted with one another in equimolar amounts. In terms of yield, it may be advantageous to employ an excess of II.1 based on III.

The starting materials-required for preparing the compounds I are known from the literature or can be prepared in accordance with the literature cited [Heterocycl. 1996, 1031-1047; Tetrahedron Lett. 24 (1966), 2661-2668], or they are commercially available.

The hydroxytriazolopyrimidines of the formula IV.1 are then reacted with a halogenating agent to give halotriazolopyrimidines of the formula V.1:

IV.1 $\xrightarrow{\text{halogenation}}$ 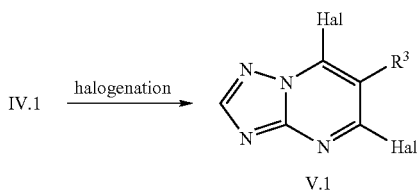
V.1

This reaction is usually carried out at temperatures of from 0° C. to 150° C., preferably from 80° C. to 125° C., in an inert organic solvent or without additional solvent [cf.EP-A-770 615].

Suitable halogenating agents are, preferably, brominating or chlorinating agents, such as, for example, phosphorus oxybromide or phosphorus oxychloride, undiluted or in the presence of a solvent.

Suitable solvents are aliphatic hydrocarbons, such as pentane, hexane, cyclohexane and petroleum ether, aromatic hydrocarbons, such as toluene, o-, m- and p-xylene, particularly preferably toluene, o-, m- and p-xylene.

It is also possible to use mixtures of the solvents mentioned.

The halotriazolopyrimidines of the formula V.1 are then reacted with an amine of the formula VI to give 7-aminotriazolopyrimidines of the formula I in which X is halogen:

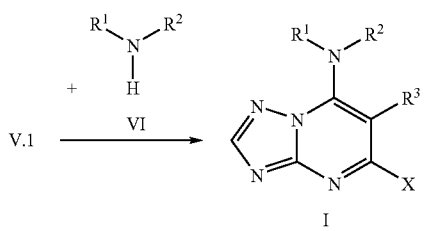

This reaction is usually carried out at temperatures of from 0° C. to 70° C., preferably from 10° C. to 35° C., in an inert organic solvent in the presence of a base [cf.EP-A-550 113].

Suitable solvents are aromatic hydrocarbons, such as toluene, o-, m- and p-xylene, halogenated hydrocarbons, such as methylene chloride, chloroform and chlorobenzene, and ethers, such as diethyl ether, diisopropyl ether, tert-butyl methyl ether, dioxane, anisole and tetrahydrofuran.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide and dimethoxymagnesium, moreover organic bases, for example tertiary amines, such as trimethylamine, triethylamine, triisopropylethylamine and N-methylpiperidine, pyridine, substituted pyridines, such as collidine, lutidine and 4-dimethylaminopyridine, and also bicyclic amines. Particular preference is given to triethylamine, potassium carbonate and sodium carbonate.

In general, the bases are employed in catalytic amounts; however, they can also be used in equimolar amounts, in excess or, if appropriate, as solvent. Alternatively, an excess of the compound VI may serve as base.

The starting materials are generally reacted with one another in equimolar amounts. In terms of yield, it may be advantageous to employ an excess of VI based on V.I.

To obtain 7-aminotriazolopyrimidines of the formula I in which X is cyano or $C_1$-$C_4$-alkoxy, 7-aminotriazolopyrimidines of the formula I are reacted with a compound of the formula VII:

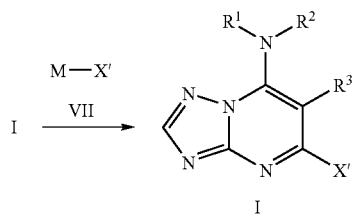

Here, M is an ammonium, tetraalkylammonium, alkali metal or alkaline earth metal cation and X' is cyano or alkoxy. This reaction is usually carried out at temperatures of from 0° C. to 150° C., preferably from 20° C. to 75° C., in an inert organic solvent [cf. WO 99/41255].

Suitable solvents are ethers, such as diethyl ether, diisopropyl ether, tert-butyl methyl ether, dioxane, anisole and tetrahydrofuran, alcohols, such as methanol, ethanol, n-propanol, isopropanol, n-butanol and tert-butanol, and also dimethyl sulfoxide, dimethylformamide and dimethylacetamide, particularly preferably diethyl ether, tetrahydrofuran, methanol and dimethylformamide.

It is also possible to use mixtures of the solvents mentioned.

The starting materials are generally reacted with one another in equimolar amounts. In terms of yield, it may be advantageous to employ an excess of VII, based on I.

7-Aminotriazolopyrimidines of the formula I in which X is $C_1$-$C_4$-haloalkyl or unsubstituted or $R^\alpha$-substituted phenyl can be obtained from dicarbonyl compounds of the formula II.2, which are cyclized with 3-amino-1,2,4-triazole of the formula III to give 7-hydroxytriazolopyrimidines of the formula IV.2:

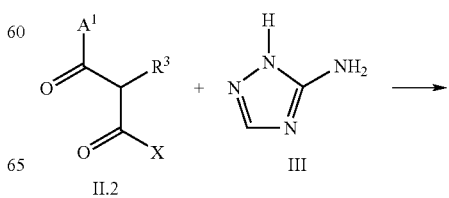

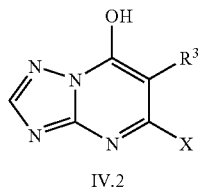

IV.2

This reaction is carried out under the same conditions as the conversion of II.1 into IV.1 described above.

The 7-hydroxytriazolopyrimidines of the formula IV.2 are then reacted with a halogenating agent to give 7-halotriazolopyrimidines of the formula V.2:

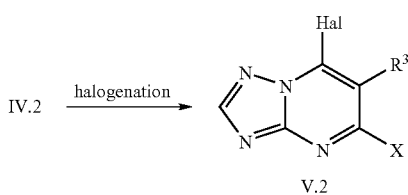

This reaction is carried out under the same conditions as the conversion of IV.1 into V.1 described above.

Compound V.2 is then reacted with an amine of the formula VI to give compounds of the formula I:

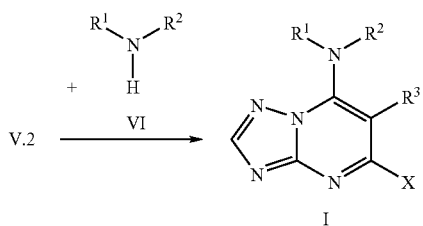

This reaction is carried out under the same conditions as the conversion of V.1 into I described above.

The reaction mixtures are worked up in a customary manner, for example by mixing with water, separation of the phases and, if appropriate, chromatographic purification of the crude products. Some of the intermediates and end products are obtained in the form of colorless or slightly brownish viscous oils which can be purified or freed from volatile components under reduced pressure and at moderately elevated temperature. If the intermediates and end products are obtained as solids, purification can also be carried out by recrystallization or digestion.

If individual compounds I are not obtainable by the routes described above, they can be prepared by derivatization of other compounds I.

7-Hydroxy- and 7-halotriazolopyrimidines of the formulae IV and V,

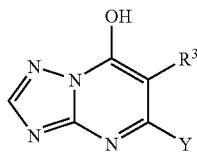

IV

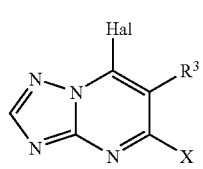

V where Y is a hydroxyl group or a radical from the group X as set forth in claim 1, Hal is halogen and $R^3$ and X are as defined in claim 1 are novel.

Particular preference is given to intermediates of the formulae IV and V, in which $R^3$ is $C_1$-$C_{10}$-alkyl, in particular $CH_3$, $CH_2$—$CH_3$, $(CH_2)_3$—$CH_3$, $CH_2$—$CH(CH_3)_2$, $CH(CH_3)$—$CH_2$—$CH_2$—$CH_3$, $C(CH_3)_3$, $(CH_2)_7$—$CH_3$, $CH(CH_3)_2$, $C_2$-$C_{10}$-alkenyl, in particular $CH_2$—$CH$=$CH_2$, $C_3$-$C_8$-cycloalkyl, in particular cyclopropylmethyl, cyclopentyl or cyclohexyl, phenyl-$C_1$-$C_{10}$-alkyl, in particular $CH_2$—$C_6H_5$, $CH_2$-o-Cl—$C_6H_4$, $C_1$-$C_{10}$-haloalkyl, in particular $CH_2$—$CF_3$, $CH(CH_3)$—$CF_3$ or $CH(CF_3)_2$, and X is halogen, in particular chlorine, cyano, $C_1$-$C_4$-alkoxy, in particular $OCH_3$, $C_1$-$C_4$-haloalkyl, in particular $CF_3$, phenyl or $R^a$-substituted phenyl, in particular phenyl.

In the definitions of the symbols given in the above formulae, collective terms were used which generally represent the following substituents:

halogen: fluorine, chlorine, bromine and iodine;

alkyl: saturated, straight-chain or branched hydrocarbon radicals having 1 to 4, 6, 8 or 10 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 10 carbon atoms (as mentioned above), where the hydrogen atoms in these groups may be partially, for example one to three times, or fully replaced by halogen atoms as mentioned above, for example $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 6 carbon atoms (as mentioned above) which are linked to the skeleton via an oxygen atom (—O—);

haloalkoxy: straight-chain or branched haloalkyl groups having 1 to 6 carbon atoms (as mentioned above) which are linked to the skeleton via an oxygen atom (—O—);

alkylthio: straight-chain or branched alkyl groups having 1 to 6 carbon atoms (as mentioned above) which are linked to the skeleton via a sulfur atom (—S—);

alkylamino: a straight-chain or branched alkyl group having 1 to 6 carbon atoms (as mentioned above) which is linked to the skeleton via an amino group (—NH—);

dialkylamino: two straight-chain or branched alkyl groups having in each case 1 to 6 carbon atoms (as mentioned above) which are independent of each other and which are linked to the skeleton via a nitrogen atom;

alkenyl: unsaturated, straight-chain or branched hydrocarbon radicals having 2 to 6 or 10 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkenyloxy: unsaturated, straight-chain or branched hydrocarbon radicals having 3 to 6 carbon atoms and a double bond in any position which is not adjacent to the hetero atom (as mentioned above) which are linked to the skeleton via an oxygen atom (—O—);

alkynyl: straight-chain or branched hydrocarbon groups having 2 to 6 or 10 carbon atoms and a triple bond in any position, for example $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkynyloxy: unsaturated, straight-chain or branched hydrocarbon radicals having 3 to 6 carbon atoms and a triple bond in any position which is not adjacent to the hetero atom (as mentioned above) which are linked to the skeleton via an oxygen atom (—O—);

cycloalkyl: monocyclic, saturated hydrocarbon groups having 3 to 5, 6 or 8 carbon ring members, for example $C_3$-$C_8$-cycloalkyl such as cyclopropyl, cyclobutyl, cyclopentyl, cyclohexyl, cycloheptyl and cyclooctyl;

5- or 6-membered heterocycles (heterocyclyl) containing, in addition to carbon ring members, one to four nitrogen atoms and/or one oxygen or sulfur atom or one oxygen and/or sulfur atom, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydro-triazin-2-yl and 1,2,4-hexahydrotriazin-3-yl;

5-membered heteroaryl, containing one to four nitrogen atoms or one to three nitrogen atoms and one sulfur or oxygen atom: heteroaryl groups having 5 ring members which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl, containing one to three or one to four nitrogen atoms: heteroaryl groups having 6 ring members which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

oxyalkyleneoxy: divalent unbranched chains of 1 to 3 $CH_2$ groups, where both valencies are attached to the skeleton via an oxygen atom, for example $OCH_2O$, $OCH_2CH_2O$ and $OCH_2CH_2CH_2O$.

The compounds of the formula I can also be present in the form of their agriculturally useful salts, the nature of the salt generally being immaterial. In general, the salts of those cations and the acid addition salts of those acids are suitable whose cations and anions, respectively, have no adverse effect on the fungicidal action of the compounds I.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di-(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of $C_1$-$C_4$-alkanoic acids, preferably formate, acetate, propionate and butyrate.

With respect to the intended use of the 7-aminotriazolopyrimidines of the formula I, particular preference is given to the following meanings of the substituents, in each case on their own or in combination:

Compounds I in which $R^1$, $R^2$ are hydrogen, $C_1$-$C_{10}$-alkyl or $C_1$-$C_6$-haloalkyl, in particular hydrogen, $C_1$-$C_6$-alkyl or $C_1$-$C_4$-haloalkyl, particularly preferably hydrogen, 1-methylpropyl, isopropyl or 1,1,1-trifluoro-2-propyl, or where $R^1$ and $R^2$ together with the linking nitrogen atom form a 5- or 6-membered ring which may contain an oxygen atom and/or may carry a $C_1$-$C_4$-alkyl radical, for example pyrrolidin-1-yl, pyrrol-1-yl, pyrazol-1-yl, imidazol-1-yl, piperidin-1-yl or morpholin-4-yl, where the radicals mentioned may be substituted by one to three radicals $R^a$, in particular by $C_1$-$C_4$-alkyl, such as, for example, methyl or ethyl.

In addition, particular preference is also given to compounds I in which $R^1$ is hydrogen, $C_1$-$C_6$-alkyl or $C_1$-$C_4$-haloalkyl and $R^2$ is hydrogen.

Very particular preference is also given to compounds I in which $R^1$ and $R^2$ are hydrogen and $R^3$ is $C_3$-$C_8$-cycloalkyl, preferably cyclopropyl, cyclopentyl or cyclohexyl.

Moreover, particular preference is given to compounds I in which $R^3$ is $C_1$-$C_8$-alkyl, in particular isopropyl or n-octyl, $C_3$-$C_6$-cycloalkyl, particularly preferably cyclopropyl, cyclopentyl or cyclohexyl, or $CH_2$—$C_6H_5$.

Particular preference is also given to compounds I in which $R^3$ is $C_3$-$C_8$-cycloalkyl, in particular $C_3$-$C_6$-cycloalkyl, particularly preferably cyclopropyl, cyclopropylmethyl, cyclopentyl or cyclohexyl, and X is cyano, $C_1$-$C_4$-alkoxy, for example $OCH_3$, $C_1$-$C_4$-haloalkyl, for example $CF_3$, or an optionally $R^a$-substituted phenylalkyl, for example $CH_2$—$C_6H_5$ or $CH_2$-o-Cl—$C_6H_4$.

Moreover, particular preference is given to compounds I in which $R^3$ is $C_3$-$C_8$-cycloalkyl, in particular $C_3$-$C_6$-cycloalkyl, with particular preference cyclopropyl, cyclopentyl or cyclohexyl, and X is halogen, in particular chlorine.

Particular preference is likewise given to compounds I in which X is halogen, such as chlorine or bromine, in particular chlorine.

With respect to their use, particular preference is given to the compounds I compiled in the tables below. Moreover, the groups mentioned for a substituent in the tables are, by themselves and independently of the combination in which they are mentioned, a particularly preferred embodiment of the substituent in question.

Table 1

Compounds of the formula I in which $R^3$ is $CH_3$ and X is Cl and the combination of the radicals $R^1$ and $R^2$ for a compound corresponds in each case to one row of Table A Table 2

Compounds of the formula I in which $R^3$ is $CH_2$—$CH_3$ and X is Cl and the combination of the radicals $R^1$ and $R^2$ for a compound corresponds in each case to one row of Table A Table 3

Compounds of the formula I in which $R^3$ is $(CH_2)_3$—$CH_3$ and X is Cl and the combination of the radicals $R^1$ and $R^2$ for a compound corresponds in each case to one row of Table A Table 4

Compounds of the formula I in which $R^3$ is $CH_2$—$CH(CH_3)_2$ and X is Cl and the combination of the radicals $R^1$ and $R^2$ for a compound corresponds in each case to one row of Table A Table 5

Compounds of the formula I in which $R^3$ is $CH(CH_3)$—$CH_2$—$CH_2$—$CH_3$ and X is Cl and the combination of the radicals $R^1$ and $R^2$ for a compound corresponds in each case to one row of Table A Table 6

Compounds of the formula I in which $R^3$ is $C(CH_3)_3$ and X is Cl and the combination of the radicals $R^1$ and $R^2$ for a compound corresponds in each case to one row of Table A Table 7

Compounds of the formula I in which $R^3$ is $(CH_2)_7$—$CH_3$ and X is Cl and the combination of the radicals $R^1$ and $R^2$ for a compound corresponds in each case to one row of Table A Table 8

Compounds of the formula I in which $R^3$ is $CH(CH_3)_2$ and X is Cl and the combination of the radicals $R^1$ and $R^2$ for a compound corresponds in each case to one row of Table A Table 9

Compounds of the formula I in which $R^3$ is cyclopentyl and X is Cl and the combination of the radicals $R^1$ and $R^2$ for a compound corresponds in each case to one row of Table A Table 10

Compounds of the formula I in which $R^3$ is cyclohexyl and X is Cl and the combination of the radicals $R^1$ and $R^2$ for a compound corresponds in each case to one row of Table A Table 11

Compounds of the formula I in which $R^3$ is $CH_2$—$C_6H_5$ and X is Cl and the combination of the radicals $R^1$ and $R^2$ for a compound corresponds in each case to one row of Table A Table 12

Compounds of the formula I in which $R^3$ is $CH_2$-o-Cl—$C_6H_4$ and X is Cl and the combination of the radicals $R^1$ and $R^2$ for a compound corresponds in each case to one row of Table A Table 13

Compounds of the formula I in which $R^3$ is $(CH_2)_2$—$CH_3$ and X is Cl and the combination of the radicals $R^1$ and $R^2$ for a compound corresponds in each case to one row of Table A Table 14

Compounds of the formula I in which $R^3$ is $CH_2$—$CH=CH_2$ and X is Cl and the combination of the radicals $R^1$ and $R^2$ for a compound corresponds in each case to one row of Table A Table 15

Compounds of the formula I in which $R^3$ is cyclopropylmethyl and X is Cl and the combination of the radicals $R^1$ and $R^2$ for a compound corresponds in each case to one row of Table A Table 16

Compounds of the formula I in which $R^3$ is $CH_2$—$CH_2$—CN and X is Cl and the combination of the radicals $R^1$ and $R^2$ for a compound corresponds in each case to one row of Table A Table 17

Compounds of the formula I in which $R^3$ is $CH_2$—$CF_3$ and X is Cl and the combination of the radicals $R^1$ and $R^2$ for a compound corresponds in each case to one row of Table A Table 18

Compounds of the formula I in which $R^3$ is $CH(CH_3)$—$CF_3$ and X is Cl and the combination of the radicals $R^1$ and $R^2$ for a compound corresponds in each case to one row of Table A Table 19

Compounds of the formula I in which $R^3$ is $CH(CF_3)_2$ and X is Cl and the combination of the radicals $R^1$ and $R^2$ for a compound corresponds in each case to one row of Table A Table 20

Compounds of the formula I in which $R^3$ is $CH_3$ and X is $CF_3$ and the combination of the radicals $R^1$ and $R^2$ for a compound corresponds in each case to one row of Table A Table 21

Compounds of the formula I in which $R^3$ is $CH_2$—$CH_3$ and X is $CF_3$ and the combination of the radicals $R^1$ and $R^2$ for a compound corresponds in each case to one row of Table A Table 22

Compounds of the formula I in which $R^3$ is $(CH_2)_3$—$CH_3$ and X is $CF_3$ and the combination of the radicals $R^1$ and $R^2$ for a compound corresponds in each case to one row of Table A Table 23

Compounds of the formula I in which $R^3$ is $CH_2$—$CH(CH_3)_2$ and X is $CF_3$ and the combination of the radicals $R^1$ and $R^2$ for a compound corresponds in each case to one row of Table A Table 24

Compounds of the formula I in which $R^3$ is $CH(CH_3)$—$CH_2$—$CH_2$—$CH_3$ and X is $CF_3$ and the combination of the radicals $R^1$ and $R^2$ for a compound corresponds in each case to one row of Table A Table 25

Compounds of the formula I in which $R^3$ is $CH(CH_3)_3$ and X is $CF_3$ and the combination of the radicals $R^1$ and $R^2$ for a compound corresponds in each case to one row of Table A Table 26

Compounds of the formula I in which $R^3$ is $(CH_2)_7$—$CH_3$ and X is $CF_3$ and the combination of the radicals $R^1$ and $R^2$ for a compound corresponds in each case to one row of Table A Table 27

Compounds of the formula I in which $R^3$ is $CH(CH_3)_2$ and X is $CF_3$ and the combination of the radicals $R^1$ and $R^2$ for a compound corresponds in each case to one row of Table A Table 28

Compounds of the formula I in which $R^3$ is cyclopentyl and X is $CF_3$ and the combination of the radicals $R^1$ and $R^2$ for a compound corresponds in each case to one row of Table A Table 29

Compounds of the formula I in which $R^3$ is cyclohexyl and X is $CF_3$ and the combination of the radicals $R^1$ and $R^2$ for a compound corresponds in each case to one row of Table A Table 30

Compounds of the formula I in which $R^3$ is $CH_2$—$C_6H_5$ and X is $CF_3$ and the combination of the radicals $R^1$ and $R^2$ for a compound corresponds in each case to one row of Table A Table 31

Compounds of the formula I in which $R^3$ is $CH_2$-p-Cl—$C_6H_4$ and X is $CF_3$ and the combination of the radicals $R^1$ and $R^2$ for a compound corresponds in each case to one row of Table A Table 32

Compounds of the formula I in which $R^3$ is $(CH_2)_2$—$CH_3$ and X is $CF_3$ and the combination of the radicals $R^1$ and $R^2$ for a compound corresponds in each case to one row of Table A Table 33

Compounds of the formula I in which $R^3$ is $CH_2$—$CH=CH_2$ and X is $CF_3$ and the combination of the radicals $R^1$ and $R^2$ for a compound corresponds in each case to one row of Table A Table 34

Compounds of the formula I in which $R^3$ is cyclopropylmethyl and X is $CF_3$ and the combination of the radicals $R^1$ and $R^2$ for a compound corresponds in each case to one row of Table A Table 35

Compounds of the formula I in which $R^3$ is $CH_2$—$CH_2$—CN and X is $CF_3$ and the combination of the radicals $R^1$ and $R^2$ for a compound corresponds in each case to one row of Table A Table 36

Compounds of the formula I in which $R^3$ is $CH_2$—$CF_3$ and X is $CF_3$ and the combination of the radicals $R^1$ and $R^2$ for a compound corresponds in each case to one row of Table A Table 37

Compounds of the formula I in which $R^3$ is $CH(CH_3)$—$CF_3$ and X is $CF_3$ and the combination of the radicals $R^1$ and $R^2$ for a compound corresponds in each case to one row of Table A Table 38

Compounds of the formula I in which $R^3$ is $CH(CF_3)_2$ and X is $CF_3$ and the combination of the radicals $R^1$ and $R^2$ for a compound corresponds in each case to one row of Table A Table 39

Compounds of the formula I in which $R^3$ is $CH_3$ and X is phenyl and the combination of the radicals $R^1$ and $R^2$ for a compound corresponds in each case to one row of Table A Table 40

Compounds of the formula I in which $R^3$ is $CH_2$—$CH_3$ and X is phenyl and the combination of the radicals $R^1$ and $R^2$ for a compound corresponds in each case to one row of Table A Table 41

Compounds of the formula I in which $R^3$ is $(CH_2)_3$—$CH_3$ and X is phenyl and the combination of the radicals. $R^1$ and $R^2$ for a compound corresponds in each case to one row of Table A Table 42

Compounds of the formula I in which $R^3$ is $CH_2$—$CH(CH_3)_2$ and X is phenyl and the combination of the radicals $R^1$ and $R^2$ for a compound corresponds in each case to one row of Table A Table 43

Compounds of the formula I in which $R^3$ is $CH(CH_3)$—$CH_2$—$CH_2$—$CH_3$ and X is phenyl and the combination of the radicals $R^1$ and $R^2$ for a compound corresponds in each case to one row of Table A Table 44

Compounds of the formula I in which $R^3$ is $CH(CH_3)_3$ and X is phenyl and the combination of the radicals $R^1$ and $R^2$ for a compound corresponds in each case to one row of Table A Table 45

Compounds of the formula I in which $R^3$ is $(CH_2)_7$—$CH_3$ and X is phenyl and the combination of the radicals $R^1$ and $R^2$ for a compound corresponds in each case to one row of Table A Table 46

Compounds of the formula I in which $R^3$ is $CH(CH_3)_2$ and X is phenyl and the combination of the radicals $R^1$ and $R^2$ for a compound corresponds in each case to one row of Table A Table 47

Compounds of the formula I in which $R^3$ is cyclopentyl and X is phenyl and the combination of the radicals $R^1$ and $R^2$ for a compound corresponds in each case to one row of Table A Table 48

Compounds of the formula I in which $R^3$ is cyclohexyl and X is phenyl and the combination of the radicals $R^1$ and $R^2$ for a compound corresponds in each case to one row of Table A Table 49

Compounds of the formula I in which $R^3$ is $CH_2$—$C_6H_5$ and X is phenyl and the combination of the radicals $R^1$ and $R^2$ for a compound corresponds in each case to one row of Table A Table 50

Compounds of the formula I in which $R^3$ is $CH_2$-p-Cl—$C_6H_4$ and X is phenyl and the combination of the radicals $R^1$ and $R^2$ for a compound corresponds in each case to one row of Table A Table 51

Compounds of the formula I in which $R^3$ is $(CH_2)_2$—$CH_3$ and X is phenyl and the combination of the radicals $R^1$ and $R^2$ for a compound corresponds in each case to one row of Table A Table 52

Compounds of the formula I in which $R^3$ is $CH_2$—$CH=CH_2$ and X is phenyl and the combination of the radicals $R^1$ and $R^2$ for a compound corresponds in each case to one row of Table A Table 53

Compounds of the formula I in which $R^3$ is cyclopropylmethyl and X is phenyl and the combination of the radicals $R^1$ and $R^2$ for a compound corresponds in each case to one row of Table A Table 54

Compounds of the formula I in which $R^3$ is —$CH_2$—$CH_2$—CN and X is phenyl and the combination of the radicals $R^1$ and $R^2$ for a compound corresponds in each case to one row of Table A Table 55

Compounds of the formula I in which $R^3$ is $CH_2$—$CF_3$ and X is phenyl and the combination of the radicals $R^1$ and $R^2$ for a compound corresponds in each case to one row of Table A Table 56

Compounds of the formula I in which $R^3$ is $CH(CH_3)$—$CF_3$ and X is phenyl and the combination of the radicals $R^1$ and $R^2$ for a compound corresponds in each case to one row of Table A Table 57

Compounds of the formula I in which $R^3$ is $CH(CF_3)_2$ and X is phenyl and the combination of the radicals $R^1$ and $R^2$ for a compound corresponds in each case to one row of Table A Table 58

Compounds of the formula I in which $R^3$ is $CH_3$ and X is CN and the combination of the radicals $R^1$ and $R^2$ for a compound corresponds in each case to one row of Table A Table 59

Compounds of the formula I in which $R^3$ is $CH_2$—$CH_3$ and X is CN and the combination of the radicals $R^1$ and $R^2$ for a compound corresponds in each case to one row of Table A Table 60

Compounds of the formula I in which $R^3$ is $(CH_2)_3$—$CH_3$ and X is CN and the combination of the radicals $R^1$ and $R^2$ for a compound corresponds in each case to one row of Table A Table 61

Compounds of the formula I in which $R^3$ is $CH_2$—$CH(CH_3)_2$ and X is CN and the combination of the radicals $R^1$ and $R^2$ for a compound corresponds in each case to one row of Table A Table 62

Compounds of the formula I in which $R^3$ is $CH(CH_3)$—$CH_2$—$CH_2$—$CH_3$ and X is CN and the combination of the radicals $R^1$ and $R^2$ for a compound corresponds in each case to one row of Table A Table 63

Compounds of the formula I in which $R^3$ is $CH(CH_3)_3$ and X is CN and the combination of the radicals $R^1$ and $R^2$ for a compound corresponds in each case to one row of Table A Table 64

Compounds of the formula I in which $R^3$ is $(CH_2)_7$—$CH_3$ and X is CN and the combination of the radicals $R^1$ and $R^2$ for a compound corresponds in each case to one row of Table A Table 65

Compounds of the formula I in which $R^3$ is $CH(CH_3)_2$ and X is CN and the combination of the radicals $R^1$ and $R^2$ for a compound corresponds in each case to one row of Table A Table 66

Compounds of the formula I in which $R^3$ is cyclopentyl and X is CN and the combination of the radicals $R^1$ and $R^2$ for a compound corresponds in each case to one row of Table A Table 67

Compounds of the formula I in which $R^3$ is cyclohexyl and X is CN and the combination of the radicals $R^1$ and $R^2$ for a compound corresponds in each case to one row of Table A Table 68

Compounds of the formula I in which $R^3$ is $CH_2$—$C_6H_5$ and X is CN and the combination of the radicals $R^1$ and $R^2$ for a compound corresponds in each case to one row of Table A Table 69

Compounds of the formula I in which $R^3$ is $CH_2$-p-Cl—$C_6H_4$ and X is CN and the combination of the radicals $R^1$ and $R^2$ for a compound corresponds in each case to one row of Table A.

Table 70

Compounds of the formula I in which $R^3$ is $(CH_2)_2$—$CH_3$ and X is CN and the combination of the radicals $R^1$ and $R^2$ for a compound corresponds in each case to one row of Table A Table 71

Compounds of the formula I in which $R^3$ is $CH_2$—$CH$=$CH_2$ and X is CN and the combination of the radicals $R^1$ and $R^2$ for a compound corresponds in each case to one row of Table A Table 72

Compounds of the formula I in which $R^3$ is cyclopropylmethyl and X is CN and the combination of the radicals $R^1$ and $R^2$ for a compound corresponds in each case to one row of Table A Table 73

Compounds of the formula I in which $R^3$ is $CH_2$—$CH_2$—CN and X is CN and the combination of the radicals $R^1$ and $R^2$ for a compound corresponds in each case to one row of Table A Table 74

Compounds of the formula I in which $R^3$ is $CH_2$—$CF_3$ and X is CN and the combination of the radicals $R^1$ and $R^2$ for a compound corresponds in each case to one row of Table A Table 75

Compounds of the formula I in which $R^3$ is $CH(CH_3)$—$CF_3$ and X is CN and the combination of the radicals $R^1$ and $R^2$ for a compound corresponds in each case to one row of Table A Table 76

Compounds of the formula I in which $R^3$ is $CH(CF_3)_2$ and X is CN and the combination of the radicals $R^1$ and $R^2$ for a compound corresponds in each case to one row of Table A Table 77

Compounds of the formula I in which $R^3$ is $CH_3$ and X is $OCH_3$ and the combination of the radicals $R^1$ and $R^2$ for a compound corresponds in each case to one row of Table A Table 78

Compounds of the formula I in which $R^3$ is $CH_2$—$CH_3$ and X is $OCH_3$ and the combination of the radicals $R^1$ and $R^2$ for a compound corresponds in each case to one row of Table A Table 79

Compounds of the formula I in which $R^3$ is $(CH_2)_3$—$CH_3$ and X is $OCH_3$ and the combination of the radicals $R^1$ and $R^2$ for a compound corresponds in each case to one row of Table A Table 80

Compounds of the formula I in which $R^3$ is $CH_2$—$CH(CH_3)_2$ and X is $OCH_3$ and the combination of the radicals $R^1$ and $R^2$ for a compound corresponds in each case to one row of Table A Table 81

Compounds of the formula I in which $R^3$ is $CH(CH_3)$—$CH_2$—$CH_2$—$CH_3$ and X is $OCH_3$ and the combination of the radicals $R^1$ and $R^2$ for a compound corresponds in each case to one row of Table A Table 82

Compounds of the formula I in which $R^3$ is $CH(CH_3)_3$ and X is $OCH_3$ and the combination of the radicals $R^1$ and $R^2$ for a compound corresponds in each case to one row of Table A Table 83

Compounds of the formula I in which $R^3$ is $(CH_2)_7$—$CH_3$ and X is $OCH_3$ and the combination of the radicals $R^1$ and $R^2$ for a compound corresponds in each case to one row of Table A Table 84

Compounds of the formula I in which $R^3$ is $CH(CH_3)_2$ and X is $OCH_3$ and the combination of the radicals $R^1$ and $R^2$ for a compound corresponds in each case to one row of Table A Table 85

Compounds of the formula I in which $R^3$ is cyclopentyl and X is $OCH_3$ and the combination of the radicals $R^1$ and $R^2$ for a compound corresponds in each case to one row of Table A Table 86

Compounds of the formula I in which $R^3$ is cyclohexyl and X is $OCH_3$ and the combination of the radicals $R^1$ and $R^2$ for a compound corresponds in each case to one row of Table A Table 87

Compounds of the formula I in which $R^3$ is $CH_2$—$C_6H_5$ and X is $OCH_3$ and the combination of the radicals $R^1$ and $R^2$ for a compound corresponds in each case to one row of Table A Table 88

Compounds of the formula I in which $R^3$ is $CH_2$-p-Cl—$C_6H_4$ and X is $OCH_3$ and the combination of the radicals $R^1$ and $R^2$ for a compound corresponds in each case to one row of Table A Table 89

Compounds of the formula I in which $R^3$ is $(CH_2)_2$—$CH_3$ and X is $OCH_3$ and the combination of the radicals $R^1$ and $R^2$ for a compound corresponds in each case to one row of Table A Table 90

Compounds of the formula I in which $R^3$ is $CH_2$—$CH$=$CH_2$ and X is $OCH_3$ and the combination of the radicals $R^1$ and $R^2$ for a compound corresponds in each case to one row of Table A Table 91

Compounds of the formula I in which $R^3$ is cyclopropylmethyl and X is $OCH_3$ and the combination of the radicals $R^1$ and $R^2$ for a compound corresponds in each case to one row of Table A Table 92

Compounds of the formula I in which $R^3$ is $CH_2$—$CH_2$—CN and X is $OCH_3$ and the combination of the radicals $R^1$ and $R^2$ for a compound corresponds in each case to one row of Table A Table 93

Compounds of the formula I in which $R^3$ is $CH_2$—$CF_3$ and X is $OCH_3$ and the combination of the radicals $R^1$ and $R^2$ for a compound corresponds in each case to one row of Table A Table 94

Compounds of the formula I in which $R^3$ is $CH(CH_3)$—$CF_3$ and X is $OCH_3$ and the combination of the radicals $R_1$ and $R^2$ for a compound corresponds in each case to one row of Table A Table 95

Compounds of the formula I in which $R^3$ is $CH(CF_3)_2$ and X is $OCH_3$ and the combination of the radicals $R^1$ and $R^2$ for a compound corresponds in each case to one row of Table A

TABLE A

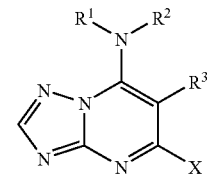

| No. | $R^1$ | $R^2$ |
|---|---|---|
| A-1 | H | H |
| A-2 | $CH_2CH_3$ | H |
| A-3 | $CH_2CH_3$ | $CH_3$ |
| A-4 | $CH_2CH_3$ | $CH_2CH_3$ |
| A-5 | $CH_2CF_3$ | H |
| A-6 | $CH_2CF_3$ | $CH_3$ |
| A-7 | $CH_2CF_3$ | $CH_2CH_3$ |
| A-8 | $CH_2CCl_3$ | H |
| A-9 | $CH_2CCl_3$ | $CH_3$ |
| A-10 | $CH_2CCl_3$ | $CH_2CH_3$ |
| A-11 | $CH_2CH_2CH_3$ | H |
| A-12 | $CH_2CH_2CH_3$ | $CH_3$ |
| A-13 | $CH_2CH_2CH_3$ | $CH_2CH_3$ |
| A-14 | $CH_2CH_2CH_3$ | $CH_2CH_2CH_3$ |
| A-15 | $CH(CH_3)_2$ | H |
| A-16 | $CH(CH_3)_2$ | $CH_3$ |
| A-17 | $CH(CH_3)_2$ | $CH_2CH_3$ |
| A-18 | (R/S) $CH(CH_3)$—$CH_2CH_3$ | H |
| A-19 | (R/S) $CH(CH_3)$—$CH_2CH_3$ | $CH_3$ |
| A-20 | (R/S) $CH(CH_3)$—$CH_2CH_3$ | $CH_2CH_3$ |
| A-21 | (R) $CH(CH_3)$—$CH_2CH_3$ | H |
| A-22 | (R) $CH(CH_3)$—$CH_2CH_3$ | $CH_3$ |
| A-23 | (R) $CH(CH_3)$—$CH_2CH_3$ | $CH_2CH_3$ |
| A-24 | (S) $CH(CH_3)$—$CH_2CH_3$ | H |
| A-25 | (S) $CH(CH_3)$—$CH_2CH_3$ | $CH_3$ |
| A-26 | (S) $CH(CH_3)$—$CH_2CH_3$ | $CH_2CH_3$ |
| A-27 | (R/S) $CH(CH_3)$—$CH(CH_3)_2$ | H |
| A-28 | (R/S) $CH(CH_3)$—$CH(CH_3)_2$ | $CH_3$ |
| A-29 | (R/S) $CH(CH_3)$—$CH(CH_3)_2$ | $CH_2CH_3$ |
| A-30 | (R) $CH(CH_3)$—$CH(CH_3)_2$ | H |
| A-31 | (R) $CH(CH_3)$—$CH(CH_3)_2$ | $CH_3$ |
| A-32 | (R) $CH(CH_3)$—$CH(CH_3)_2$ | $CH_2CH_3$ |
| A-33 | (S) $CH(CH_3)$—$CH(CH_3)_2$ | H |
| A-34 | (S) $CH(CH_3)$—$CH(CH_3)_2$ | $CH_3$ |
| A-35 | (S) $CH(CH_3)$—$CH(CH_3)_2$ | $CH_2CH_3$ |
| A-36 | (R/S) $CH(CH_3)$—$C(CH_3)_3$ | H |
| A-37 | (R/S) $CH(CH_3)$—$C(CH_3)_3$ | $CH_3$ |
| A-38 | (R/S) $CH(CH_3)$—$C(CH_3)_3$ | $CH_2CH_3$ |
| A-39 | (R) $CH(CH_3)$—$C(CH_3)_3$ | H |
| A-40 | (R) $CH(CH_3)$—$C(CH_3)_3$ | $CH_3$ |
| A-41 | (R) $CH(CH_3)$—$C(CH_3)_3$ | $CH_2CH_3$ |
| A-42 | (S) $CH(CH_3)$—$C(CH_3)_3$ | H |
| A-43 | (S) $CH(CH_3)$—$C(CH_3)_3$ | $CH_3$ |
| A-44 | (S) $CH(CH_3)$—$C(CH_3)_3$ | $CH_2CH_3$ |
| A-45 | (R/S) $CH(CH_3)$—$CF_3$ | H |
| A-46 | (R/S) $CH(CH_3)$—$CF_3$ | $CH_3$ |
| A-47 | (R/S) $CH(CH_3)$—$CF_3$ | $CH_2CH_3$ |
| A-48 | (R) $CH(CH_3)$—$CF_3$ | H |
| A-49 | (R) $CH(CH_3)$—$CF_3$ | $CH_3$ |
| A-50 | (R) $CH(CH_3)$—$CF_3$ | $CH_2CH_3$ |
| A-51 | (S) $CH(CH_3)$—$CF_3$ | H |
| A-52 | (S) $CH(CH_3)$—$CF_3$ | $CH_3$ |
| A-53 | (S) $CH(CH_3)$—$CF_3$ | $CH_2CH_3$ |
| A-54 | (R/S) $CH(CH_3)$—$CCl_3$ | H |
| A-55 | (R/S) $CH(CH_3)$—$CCl_3$ | $CH_3$ |
| A-56 | (R/S) $CH(CH_3)$—$CCl_3$ | $CH_2CH_3$ |
| A-57 | (R) $CH(CH_3)$—$CCl_3$ | H |
| A-58 | (R) $CH(CH_3)$—$CCl_3$ | $CH_3$ |
| A-59 | (R) $CH(CH_3)$—$CCl_3$ | $CH_2CH_3$ |
| A-60 | (S) $CH(CH_3)$—$CCl_3$ | H |
| A-61 | (S) $CH(CH_3)$—$CCl_3$ | $CH_3$ |
| A-62 | (S) $CH(CH_3)$—$CCl_3$ | $CH_2CH_3$ |

TABLE A-continued

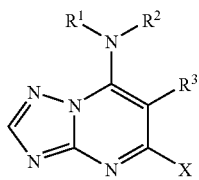

| No. | R¹ | R² |
|---|---|---|
| A-63 | CH₂C(CH₃)=CH₂ | H |
| A-64 | CH₂C(CH₃)=CH₂ | CH₃ |
| A-65 | CH₂C(CH₃)=CH₂ | CH₂CH₃ |
| A-66 | cyclopentyl | H |
| A-67 | cyclopentyl | CH₃ |
| A-68 | cyclopentyl | CH₂CH₃ |
| A-69 | —(CH₂)₂CH(CH₃)(CH₂)₂— | |

The particularly preferred embodiments of the intermediates with respect to the variables correspond to those of the radicals $R^1$, $R^2$, $R^a$, $R^3$ and X of formula I.

The compounds I are suitable for use as fungicides. They have excellent activity against a broad spectrum of phytopathogenic fungi, in particular from the class of the *Ascomycetes, Deuteromycetes, Phycomycetes* and *Basidiomycetes*. Some of them have systemic activity and can be used in crop protection as foliar and soil fungicides.

They are especially important for controlling a large number of fungi in a variety of crop plants such as wheat, rye, barley, oats, rice, maize, grass, bananas, cotton, soybean, coffee, sugar cane, grapevines, fruit species, ornamentals and vegetable species such as cucumbers, beans, tomatoes, potatoes and cucurbits, and also in the seeds of these plants.

Specifically, they are suitable for controlling the following plant diseases:

*Alternaria* species, *Podosphaera* species, *Sclerotinia* species, Physalospora canker in vegetables and fruit,
*Botrytis cinerea* (gray-mold) in strawberries, vegetables, ornamentals and grapevines,
*Corynespora cassiicola* in cucumbers,
*Colletotrichum* species in fruit and vegetables,
*Diplocarpon rosae* in roses,
*Elsinoe fawcetti* and *Diaporthe citri* in citrus fruits,
*Sphaerotheca* species in cucurbits, strawberries and roses,
*Cercospora* species in groundnuts, sugar beet and eggplants,
*Erysiphe cichoracearum* in cucurbits,
*Leveillula taurica* in bell peppers, tomatoes and eggplants,
*Mycosphaerella* species in apples and Japanese apricot,
*Phyllactinia kakicola, Gloesporium kaki,* in Japanese apricot,
*Gymnosporangium yamadae, Leptothyrium pomi, Podosphaera leucotricha* and *Gloedes pomigena* in apples,
*Cladosporium carpophilum* in pears and Japanese apricot,
*Phomopsis* species in pears,
*Phytophthora* species in citrus fruits, potatoes, onions, in particular Phytophthora infestans in potatoes and tomatoes,
*Blumeria graminis* (powdery mildew) in cereals,
*Fusarium* and *Verticillium* species in a variety of plants,
*Glomerella cingulata* in tea,
*Drechslera* and *Bipolaris* species in cereals and rice,
*Mycosphaerella* species in bananas and groundnuts,
*Plasmopara viticola* in grapevines,
*Personospora* species in onions, spinach and chrysanthemums,
*Phaeoisariopsis vitis* and *Sphaceloma ampelina* in grapefruits,
*Pseudocercosporella herpotrichoides* in wheat and barley,
*Pseudoperonospora* species in hops and cucumbers,
*Puccinia* species and *Typhula* species in cereals and lawn,
*Pyricularia oryzae* in rice,
*Rhizoctonia species* in cotton, rice and lawn,
*Stagonospora nodorum* and *Septoria tritici* in wheat,
*Uncinula necator* in grapevines,
*Ustilago* species in cereals and sugar cane, and also
*Venturia* species (scab) in apples and pears.

The compounds I are also suitable for controlling harmful fungi such as Paecilomyces variotii in the protection of materials (for example wood, paper, paint dispersions, fibers or tissues) and in the protection of stored products.

The compounds I are employed by treating the fungi or the plants, seeds, materials or the soil to be protected against fungal attack with a fungicidally effective amount of the active compounds. The application can be carried out before or after the infection of the materials, plants or seeds by the fungi.

The fungicidal compositions generally comprise from 0.1 to 95, preferably from 0.5 to 90, % by weight of active compound.

For use in crop protection, the application rates are, depending on the kind of effect desired, from 0.01 to 2 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compounds I can be converted into the customary formulations, e.g. solutions, emulsions, suspensions, dusts, powders, pastes and granules. The use form depends on the specific intended use; in any case, it should ensure fine and uniform distribution of the compound according to the invention.

The formulations are prepared in a known manner, e.g. by extending the active compound with solvents and/or carriers, if desired using emulsifiers and dispersants, it being possible to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates), and dispersants such as lignosulfite waste liquors and methylcellulose.

Suitable surfactants are the alkali metal, alkaline earth metal and ammonium salts of lignosulfonic acid, naphthalenesulfonic acid, phenolsulfonic acid, and dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for preparing directly sprayable solutions, emulsions, pastes or oil dispersions are petroleum fractions having medium to high boiling points, such as kerosene or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or joint grinding the active substances with a solid carrier.

Granules, for example coated granules, impregnated granules and homogenous granules, can be prepared by binding the active compounds to solid carriers. Solid carriers are, for example, mineral earths, such as silica gel, silicas, silicates, talc, kaolin, atta clay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

Examples of formulations are:
I. 5 parts by weight of a compound according to the invention are thoroughly mixed with 95 parts by weight of finely divided kaolin. This affords a dusting composition comprising 5% by weight of the active compound.
II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).
III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).
IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).
V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).
VI. 90 parts by weight of a compound according to the invention are mixed with 10 parts by weight of N-methyl-α-pyrrolidone, affording a solution which is suitable for use in the form of very small drops (active compound content 90% by weight
VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100 000 parts by weight of water and finely dispersed therein, affording an aqueous dispersion comprising 0.02% by weight of active compound.
VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20 000 parts by weight of water, affording a spray liquor comprising 0.1% by weight of active compound.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should ensure very fine dispersion of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with a high degree of success in the ultra-low-volume (ULV) method, it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, a mixture of the compounds I, or of the compositions comprising them, in the use form as fungicides with other fungicides results in a broader fungicidal spectrum of activity.

The following list of fungicides in combination with which the compounds according to the invention can be used is intended to illustrate the possible combinations, but not to impose any limitations:

sulfur, dithiocarbamates and their derivatives, such as iron (III)dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl) disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2-chloro-N-(4'-chlorobiphenyl-2-yl)nicotinamide, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))-benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolyl urea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis-(3-methoxycarbonyl-2-thioureido)benzene, strobilurins, such as methyl E-methoximino-[α-(o-tolyloxy)-o-tolyl]acetate, methyl E-2-{2-[6-(2-cyanophenoxy)pyridimin-4-yloxy]phenyl}-3-methoxyacrylate, methyl-E-methoxyimino-[α-(2-phenoxyphenyl)]acetamide, methyl-E-methoxyimino-[α-(2,5-dimethylphenoxy) tolyl]-acetamide, methyl E-2-{2-[2-trifluoromethylpyrid-6-yl]oxymethyl]phenyl}-3-methoxyacrylate, methyl (E,E)-methoximino-{2-[1-(3-trifluoromethylphenyl)ethylidene-aminooxymethyl]phenyl}acetate, methyl N-(2-{[1-(4-chlorophenyl)-1H-pyrazol-3-yl] oxymethyl}phenyl)-N-methoxycarbamate, anilinopyrimidines, such as N-(4,6-dimethylpyrimidin-2-yl) aniline, N-[4-methyl-6-(1-propynyl)pyrimidin-2-yl] aniline, N-(4-methyl-6-cyclopropylpyrimidin-2-yl) aniline, phenylpyrroles, such as 4-(2,2-difluoro-1,3-benzodioxol-4-yl)pyrrole-3-carbonitrile, cinnamamides, such as 3-(4-chlorophenyl)-3-(3,4-dimethoxy-phenyl)acryloylmorpholide, 3-(4-fluorophenyl)-3-(3,4-dimethoxy-phenyl)acryloylmorpholide, and a variety of fungicides, such as dodecylguanidine acetate, 1-(3-bromo-6-methoxy-2-methylphenyl)-1-(2,3,4-trimethoxy-6-methylphenyl)methanone, 3-[3-(3,5-dimethyl-2-oxycyclohexyl)-2-hydroxyethyl]-glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzohydryl alcohol, N-(3-chloro-2,6-dinitro-4-trifluoromethylphenyl)-5-trifluoromethyl-3-chloro-2-aminopyridine, 1-((bis-(4-fluorophenyl) methylsilyl)-methyl)-1H-1,2,4-triazole, N,N-dimethyl-5-chloro-2-cyano-4-p-tolylimidazole-1-sulfonamide, 3,5-dichloro-N-(3-chloro-1-ethyl-1-methyl-2-oxopropyl)-4-methylbenzamide.

SYNTHESIS EXAMPLES

The procedures given in the synthesis examples below were used to obtain further compounds I by appropriate modification of the starting materials. The compounds obtained in this manner are listed in the table that follows, together with physical data.

Example 1

Preparation of 5,7-dihydroxy-6-isopropyl-[1,2,4]-triazolo-[1,5-α]-pyrimidine

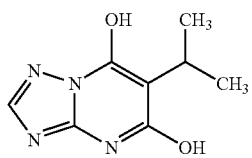

A mixture of 14 g (0.17 mol) of 3-amino-1,2,4-triazole, 34.3 g (0.17 mol) of diethyl 2-isopropylmalonate and 50 ml of tributylamine were stirred at 180° C. for 6 h. The reaction mixture was then cooled to 70° C., an aqueous solution of sodium hydroxide (21 g/200 ml of water) was added and the mixture was stirred for 30 min. The organic phase was separated and the aqueous phase was extracted with diethyl ether. The aqueous phase was then acidified using conc. hydrochloric acid and the resulting precipitate was collected by filtration. Drying gave 27 g (0.14 mol) of the title compound.

Example 2

Preparation of 5,7-dichloro-6-isopropyl-[1,2,4]-triazolo-[1,5-α]-pyrimidine

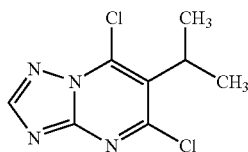

A mixture of 25 g (0.13 mol) of 5,7-dichloro-6-isopropyl-[1,2,4]-triazolo[1,5-α]-pyrimidine (cf. Ex. 1) and 50 ml of phosphorus oxychloride was refluxed for 8 h. Some of the phosphorus oxychloride was then distilled off, and the residue was poured into a mixture of methylene chloride and water. The organic phase was separated off, dried and filtered. The filtrate was freed from the solvent. This gave 16 g (0.07 mol) of the title compound (melting point 119° C.).

Example 3

Preparation of 5-chloro-6-isopropyl-7-cyclopentylamino-[1,2,4]-triazolo-[1,5-α]-pyrimidine

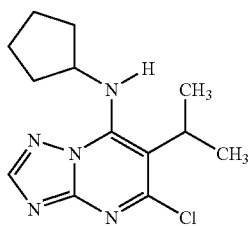

With stirring, a mixture of 0.13 g (1.5 mmol) of cyclopentylamine and 0.15 g (1.5 mmol) of triethylamine in 10 ml of methylene chloride was added to a mixture of 0.34 g (1.5 mmol) of 5,7-dichloro-6-isopropyl-[1,2,4]-triazolo-[1,5-α]-pyrimidine (cf. Ex. 2) in 20 ml of methylene chloride. The reaction mixture was stirred at room temperature for 16 h and then washed with 5% strength hydrochloric acid. The organic phase was separated off, dried over sodium sulfate and filtered. The filtrate was freed from the solvent and the residue was purified chromatographically. This gave 0.32 g (1.14 mmol) of the title compound (melting point 139° C.).

Example 4

Preparation of 7-hydroxy-6-propyl-5-trifluoromethyl-[1,2,4]-triazolo[1,5-α]-pyrimidine

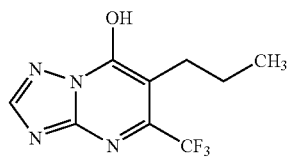

A mixture of 14 g (0.17 mol) 3-amino-1,2,4-triazole, 38.4 g (0.17 mol) of 3-oxo-2-propyl-4,4,4-trifluorobutanoate and 50 ml of tributylamine were stirred at 180° C. for 6 h. Work-up was carried out analogously to Ex. 1. Drying gave 33 g (0.13 mol) of the title compound.

Example 5

Preparation of 7-chloro-6-propyl-5-trifluoromethyl-[1,2,4]-triazolo-[1,5-α]-pyrimidine

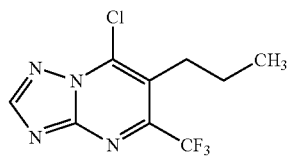

A mixture of 25 g (0.10 mol) of 5,7-dichloro-6-isopropyl-[1,2,4]-triazolo[1,5-α]-pyrimidine (cf. Ex. 4) and 50 ml of phosphorus oxychloride was heated under reflux for 8 h. Work-up was carried out analogously to Ex. 2. This gave 23 g (0.086 mol) of the title compound (melting point 63° C.).

Example 6

Preparation of 7-cyclopentylamino-6-propyl-5-trifluoromethyl-[1,2,4]-triazolo-[1,5-α]-pyrimidine

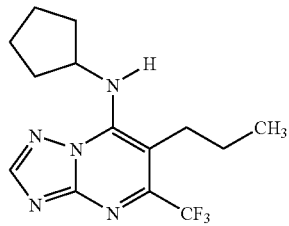

With stirring, a mixture of 0.13 g (1.5 mmol) of cyclopentylamine and 0.15 g (1.5 mmol) of triethylamine in 10 ml of methylene chloride was added to a mixture of 0.40 g (1.5 mmol) of 7-chloro-6-propyl-5-trifluoromethyl-[1,2,4]-triazolo-[1,5-α]-pyrimidine (cf. Ex. 5) in 20 ml of methylene chloride. The reaction mixture was stirred at room temperature for 16 h, work-up was carried out analogously to Ex. 3. This gave 0.39 g (1.24 mmol) of the title compound (melting point 179° C.).

Example 7

Preparation of 7-hydroxy-6-octyl-5-phenyl-[1,2,4]-triazolo-[1,5-α]-pyrimidine

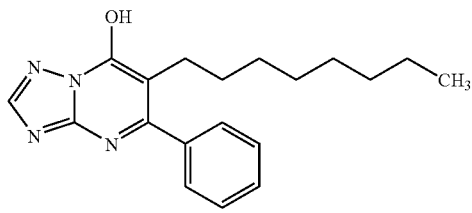

A mixture of 14.0 g (0.17 mol) of 3-amino-1,2,4-triazole, 51.7 g (0.17 mol) of 3-oxo-2-octyl-4-phenylbutanoate and 3. g of p-toluenesulfonic acid was heated under reflux for 6 h. Work-up was carried out analogously to Ex. 1. Drying gave 37 g (0.11 mol) of the title compound.

Example 8

Preparation of 7-chloro-6-octyl-5-phenyl-[1,2,4]-triazolo-[1,5-α]-pyrimidine

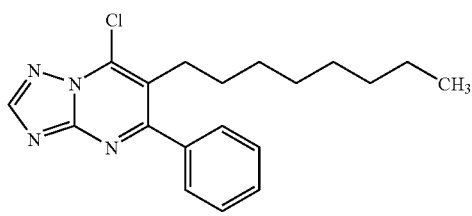

A mixture of 17 g (0.05 mol) of 7-hydroxy-6-octyl-5-phenyl-[1,2,4]-triazolo-[1,5-α]-pyrimidine (cf. Ex. 7) and 50 ml of phosphorus oxychloride was heated under reflux for 8 h. Work-up was carried out analogously to Ex. 2. This gave 16 g (0.046 mol) of the title compound.

Example 9

Preparation of 7-cyclopentylamino-6-octyl-5-phenyl-[1,2,4]-triazolo-[1,5-α]-pyrimidine

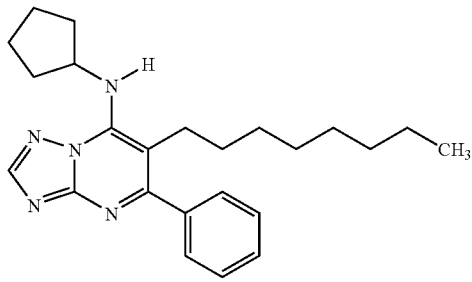

With stirring, a mixture of 0.13 g (1.5 mmol) of cyclopentylamine and 0.15 g (1.5 mmol) of triethylamine in 10 ml of methylene chloride was added to a mixture of 0.52 g (1.5 mmol) of 7-chloro-6-octyl-5-phenyl-[1,2,4]-triazolo-[1,5-α]-pyrimidine (cf. Ex. 8) in 20 ml of methylene chloride. The reaction mixture was stirred at room temperature for 16 h, work-up was carried out analogously to Ex. 3. This gave 0.52 g (1.3 mmol) of the title compound (melting point 81° C.).

Example 10

Preparation of 5-cyano-6-octyl-7-diethylamino-[1,2,4]-triazolo-[1,5-a]-pyrimidine [I-167]

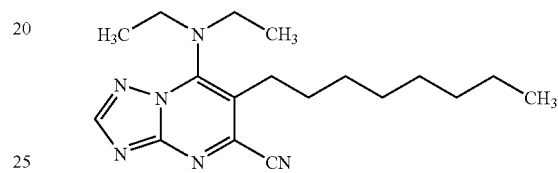

A mixture of 0.1 mol of the compound I-48 and 0.25 mol of tetraethylammonium cyanide in 750 ml of dimethylformamide was stirred at 20-25° C. for about 16 hours. Water and methyl tert-butyl ether were added, and the phases were then separated. The organic phase was washed with water and dried, and the solvent was then removed. The residue gave, after chromatography on silica gel, 8.33 g of the title compound.

$^1$H-NMR: δ in ppm: 8.5 (s); 3.65 (q); 2.9 (m); 1.7 (m); 1.3 (m); 1.2 (t); 0.9 (t).

Example 11

Preparation of 5-methoxy-6-octyl-7-diethylamino-[1,2,4]-triazolo-[1,5-α]-pyrimidine [I-168]

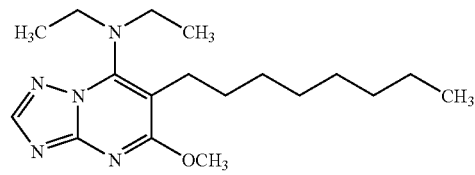

At 20-25° C., 71.5 mmol of a 30% strength sodium methoxide solution were added to a solution of 65 mmol of the compound I-48 in 400 ml of anhydrous methanol, and the mixture was then stirred at 20-25° C. for about 16 hours. The solvent was distilled off and the residue was then taken up in dichloromethane. This solution was washed with water and then dried, and the solvent was removed. Chromatography on silica gel gave 7.5 g of the title compound.

$^1$H-NMR: δ in ppm: 8.18 (s); 4.09 (s); 3.41 (q); 2.65 (m); 1.55 (m); 1.3 (m); 1.1 (t); 0.9 (t).

TABLE 1

| No. | R$^1$ | R$^2$ | R$^3$ | X | phys. data (m.p. [° C.]; IR[cm$^{-1}$]; $^1$H-NMR δ [ppm] |
|---|---|---|---|---|---|
| I-1 | CH(CH$_3$)$_2$ | H | CH$_3$ | Cl | 169 |
| I-2 | —(CH$_2$)$_2$CH(CH$_3$)(CH$_2$)$_2$— | | CH$_3$ | Cl | 125 |
| I-3 | cyclopentyl | H | CH$_3$ | Cl | 172 |
| I-4 | CH$_2$—CH$_3$ | CH$_2$—CH$_3$ | CH$_3$ | Cl | 96 |
| I-5 | CH(CH$_3$)—CF$_3$ | H | CH$_3$ | Cl | 209 |
| I-6 | CH$_2$—CF$_3$ | H | CH$_3$ | Cl | 133 |
| I-7 | CH$_2$—C(CH$_3$)=CH$_2$ | CH$_2$—CH$_3$ | CH$_2$—CH$_3$ | Cl | 55 |
| I-8 | CH(CH$_3$)$_2$ | H | CH$_2$—CH$_3$ | Cl | 152 |
| I-9 | —(CH$_2$)$_2$CH(CH$_3$)(CH$_2$)$_2$— | | CH$_2$—CH$_3$ | Cl | 1543, 1521, 1451 |
| I-10 | cyclopentyl | H | CH$_2$—CH$_3$ | Cl | 136 |
| I-11 | CH$_2$—CH$_3$ | CH$_2$—CH$_3$ | CH$_2$—CH$_3$ | Cl | 1596, 1511, 1464 |
| I-12 | (CH$_2$)$_2$—CH$_3$ | (CH$_2$)$_2$—CH$_3$ | CH$_2$—CH$_3$ | Cl | 1595, 1511, 1456 |
| I-13 | CH—(CH$_3$)$_2$ | CH$_3$ | CH$_2$—CH$_3$ | Cl | 1593, 1513, 1097 |
| I-14 | (R/S)CH(CH$_3$)—CH$_2$—CH$_3$ | H | CH$_2$—CH$_3$ | Cl | 145 |
| I-15 | (R)CH(CH$_3$)—CH$_2$—CH$_3$ | H | CH$_2$—CH$_3$ | Cl | 140 |
| I-16 | (S)CH(CH$_3$)—CH$_2$—CH$_3$ | H | CH$_2$—CH$_3$ | Cl | 140 |
| I-17 | (R/S)CH(CH$_3$)—CH(CH$_3$)$_2$ | H | CH$_2$—CH$_3$ | Cl | 119 |
| I-18 | (R)CH(CH$_3$)—CH(CH$_3$)$_2$ | H | CH$_2$—CH$_3$ | Cl | 102 |
| I-19 | (S)CH(CH$_3$)—CH(CH$_3$)$_2$ | H | CH$_2$—CH$_3$ | Cl | 102 |
| I-20 | (R/S)CH(CH$_3$)—C(CH$_3$)$_3$ | H | CH$_2$—CH$_3$ | Cl | 116 |
| I-21 | (R)CH(CH$_3$)—C(CH$_3$)$_3$ | H | CH$_2$—CH$_3$ | Cl | 1613, 1555, 1464 |
| I-22 | (S)CH(CH$_3$)—C(CH$_3$)$_3$ | H | CH$_2$—CH$_3$ | Cl | 1612, 1554, 1464 |
| I-23 | (R/S)CH(CH$_3$)—CF$_3$ | H | CH$_2$—CH$_3$ | Cl | 169 |
| I-24 | (R)CH(CH$_3$)—CF$_3$ | H | CH$_2$—CH$_3$ | Cl | 140 |
| I-25 | (S)CH(CH$_3$)—CF$_3$ | H | CH$_2$—CH$_3$ | Cl | 140 |
| I-26 | H | H | CH$_2$—CH$_3$ | Cl | 263 |
| I-27 | —(CH$_2$)$_2$CH(CH$_3$)(CH$_2$)$_2$— | | (CH$_2$)$_3$—CH$_3$ | Cl | 91 |
| I-28 | (R/S)CH(CH$_3$)—CF$_3$ | H | (CH$_2$)$_3$—CH$_3$ | Cl | 125 |
| I-29 | (R)CH(CH$_3$)—CF$_3$ | H | (CH$_2$)$_3$—CH$_3$ | Cl | 121 |
| I-30 | (S)CH(CH$_3$)—CF$_3$ | H | (CH$_2$)$_3$—CH$_3$ | Cl | 121 |
| I-31 | CH$_2$—CF$_3$ | H | (CH$_2$)$_3$—CH$_3$ | Cl | 156 |
| I-32 | CH$_2$—C(CH$_3$)=CH$_2$ | H | CH$_2$—CH(CH$_3$)$_2$ | Cl | 180 |
| I-33 | CH(CH$_3$)$_2$ | H | CH$_2$—CH(CH$_3$)$_2$ | Cl | 127 |
| I-34 | cyclopentyl | H | CH$_2$—CH(CH$_3$)$_2$ | Cl | 56 |
| I-35 | CH$_2$CH$_3$ | CH$_2$CH$_3$ | CH$_2$—CH(CH$_3$)$_2$ | Cl | 163 |
| I-36 | CH(CH$_3$)—CH$_2$—CH$_3$ | H | CH$_2$—CH(CH$_3$)$_2$ | Cl | 159 |
| I-37 | CH(CH$_3$)$_2$ | H | CH(CH$_3$)—CH$_2$—CH$_2$—CH$_3$ | Cl | 180 |
| I-38 | cyclopentyl | H | CH(CH$_3$)—CH$_2$—CH$_2$—CH$_3$ | Cl | 127 |
| I-39 | CH$_2$CH$_3$ | CH$_2$CH$_3$ | CH(CH$_3$)—CH$_2$—CH$_2$—CH$_3$ | Cl | 56 |
| I-40 | (R/S)CH(CH$_3$)—CF$_3$ | H | CH(CH$_3$)—CH$_2$—CH$_2$—CH$_3$ | Cl | 163 |
| I-41 | CH$_2$—CF$_3$ | H | CH(CH$_3$)—CH$_2$—CH$_2$—CH$_3$ | Cl | 159 |
| I-42 | CH(CH$_3$)$_2$ | H | C(CH$_3$)$_3$ | Cl | 136 |
| I-43 | —(CH$_2$)$_2$CH(CH$_3$)(CH$_2$)$_2$— | | C(CH$_3$)$_3$ | Cl | 140 |
| I-44 | CH$_2$—C(CH$_3$)=CH$_2$ | CH$_2$—CH$_3$ | (CH$_2$)$_7$—CH$_3$ | Cl | 2927, 1597, 1508, 1462 |
| I-45 | CH(CH$_3$)$_2$ | H | (CH$_2$)$_7$—CH$_3$ | Cl | 2926, 1613, 1553, 1464 |
| I-46 | —(CH$_2$)$_2$CH(CH$_3$)(CH$_2$)$_2$— | | (CH$_2$)$_7$—CH$_3$ | Cl | 2925, 1594, 1520, 1192 |
| I-47 | cyclopentyl | H | (CH$_2$)$_7$—CH$_3$ | Cl | 2927, 1612, 1554, 1059 |
| I-48 | CH$_2$—CH$_3$ | CH$_2$—CH$_3$ | (CH$_2$)$_7$—CH$_3$ | Cl | 2927, 1598, 1511, 1466 |
| I-49 | (CH$_2$)$_2$—CH$_3$ | (CH$_2$)$_2$—CH$_3$ | (CH$_2$)$_7$—CH$_3$ | Cl | 2927, 1597, 1561, 1457 |
| I-50 | CH—(CH$_3$)$_2$ | CH$_3$ | (CH$_2$)$_7$—CH$_3$ | Cl | 2926, 1595, 1514, 1467 |
| I-51 | (R/S)CH(CH$_3$)—CH(CH$_3$)$_2$ | H | (CH$_2$)$_7$—CH$_3$ | Cl | 2926, 1613, 1553, 1464 |
| I-52 | (R)CH(CH$_3$)—CH(CH$_3$)$_2$ | H | (CH$_2$)$_7$—CH$_3$ | Cl | 2926, 1612, 1553, 1464 |
| I-53 | (S)CH(CH$_3$)—CH(CH$_3$)$_2$ | H | (CH$_2$)$_7$—CH$_3$ | Cl | 2926, 1612, 1552, 1463 |
| I-54 | (R/S)CH(CH$_3$)—C(CH$_3$)$_3$ | H | (CH$_2$)$_7$—CH$_3$ | Cl | 2926, 1613, 1555, 1464 |
| I-55 | (R)CH(CH$_3$)—C(CH$_3$)$_3$ | H | (CH$_2$)$_7$—CH$_3$ | Cl | 2926, 1613, 1556, 1467 |
| I-56 | (S)CH(CH$_3$)—C(CH$_3$)$_3$ | H | (CH$_2$)$_7$—CH$_3$ | Cl | 2925, 1612, 1556, 1466 |
| I-57 | (R/S)CH(CH$_3$)—CF$_3$ | H | (CH$_2$)$_7$—CH$_3$ | Cl | 1619, 1533, 1146 |
| I-58 | (R)CH(CH$_3$)—CF$_3$ | H | (CH$_2$)$_7$—CH$_3$ | Cl | 1620, 1542, 1146 |
| I-59 | (S)CH(CH$_3$)—CF$_3$ | H | (CH$_2$)$_7$—CH$_3$ | Cl | 1619, 1541, 1146 |
| I-60 | CH$_2$—C(CH$_3$)=CH$_2$ | CH$_2$—CH$_3$ | CH(CH$_3$)$_2$ | Cl | 71 |
| I-61 | CH(CH$_3$)$_2$ | H | CH(CH$_3$)$_2$ | Cl | 180 |
| I-62 | CH$_2$—CH$_3$ | CH$_2$—CH$_3$ | CH(CH$_3$)$_2$ | Cl | 91 |
| I-63 | (CH$_2$)$_2$—CH$_3$ | (CH$_2$)$_2$—CH$_3$ | CH(CH$_3$)$_2$ | Cl | 1592, 1506, 1454 |
| I-64 | CH—(CH$_3$)$_2$ | CH$_3$ | CH(CH$_3$)$_2$ | Cl | 85 |
| I-65 | (R/S)CH(CH$_3$)—CH$_2$—CH$_3$ | H | CH(CH$_3$)$_2$ | Cl | 1616, 1544, 1463 |
| I-66 | (R)CH(CH$_3$)—CH$_2$—CH$_3$ | H | CH(CH$_3$)$_2$ | Cl | 160 |
| I-67 | (S)CH(CH$_3$)—CH$_2$—CH$_3$ | H | CH(CH$_3$)$_2$ | Cl | 160 |
| I-68 | (R/S)CH(CH$_3$)—CH(CH$_3$)$_2$ | H | CH(CH$_3$)$_2$ | Cl | 134 |
| I-69 | (R)CH(CH$_3$)—CH(CH$_3$)$_2$ | H | CH(CH$_3$)$_2$ | Cl | 120 |
| I-70 | (S)CH(CH$_3$)—CH(CH$_3$)$_2$ | H | CH(CH$_3$)$_2$ | Cl | 120 |
| I-71 | (R/S)CH(CH$_3$)—C(CH$_3$)$_3$ | H | CH(CH$_3$)$_2$ | Cl | 2964, 1611, 1551 |
| I-72 | (R)CH(CH$_3$)—C(CH$_3$)$_3$ | H | CH(CH$_3$)$_2$ | Cl | 64 |
| I-73 | (S)CH(CH$_3$)—C(CH$_3$)$_3$ | H | CH(CH$_3$)$_2$ | Cl | 64 |
| I-74 | (R/S)CH(CH$_3$)—CF$_3$ | H | CH(CH$_3$)$_2$ | Cl | 1616, 1527, 1147 |
| I-75 | (R)CH(CH$_3$)—CF$_3$ | H | CH(CH$_3$)$_2$ | Cl | 70 |

TABLE 1-continued

| No. | R$^1$ | R$^2$ | R$^3$ | X | phys. data (m.p. [° C.]; IR[cm$^{-1}$]; $^1$H-NMR δ [ppm] |
|---|---|---|---|---|---|
| I-76 | (S)CH(CH$_3$)—CF$_3$ | H | CH(CH$_3$)$_2$ | Cl | 70 |
| I-77 | H | H | CH(CH$_3$)$_2$ | Cl | 271 |
| I-78 | CH$_2$—C(CH$_3$)=CH$_2$ | CH$_2$—CH$_3$ | cyclopentyl | Cl | 66 |
| I-79 | CH(CH$_3$)$_2$ | H | cyclopentyl | Cl | 136 |
| I-80 | CH$_2$—CH$_3$ | CH$_2$—CH$_3$ | cyclopentyl | Cl | 78 |
| I-81 | (CH$_2$)$_2$—CH$_3$ | (CH$_2$)$_2$—CH$_3$ | cyclopentyl | Cl | 87 |
| I-82 | CH$_2$—C(CH$_3$)=CH$_2$ | CH$_2$—CH$_3$ | cyclohexyl | Cl | 136 |
| I-83 | CH(CH$_3$)$_2$ | H | cyclohexyl | Cl | 156 |
| I-84 | —(CH$_2$)$_2$CH(CH$_3$)(CH$_2$)$_2$— | | cyclohexyl | Cl | 151 |
| I-85 | cyclopentyl | H | cyclohexyl | Cl | 158 |
| I-86 | CH$_2$—CH$_3$ | CH$_2$—CH$_3$ | cyclohexyl | Cl | 103 |
| I-87 | (CH$_2$)$_2$—CH$_3$ | (CH$_2$)$_2$—CH$_3$ | cyclohexyl | Cl | 139 |
| I-88 | CH—(CH$_3$)$_2$ | CH$_3$ | cyclohexyl | Cl | 134 |
| I-89 | (R/S)CH(CH$_3$)—CH$_2$—CH$_3$ | H | cyclohexyl | Cl | 155 |
| I-90 | (R)CH(CH$_3$)—CH$_2$—CH$_3$ | H | cyclohexyl | Cl | 155 |
| I-91 | (S)CH(CH$_3$)—CH$_2$—CH$_3$ | H | cyclohexyl | Cl | 155 |
| I-92 | (R/S)CH(CH$_3$)—CH(CH$_3$)$_2$ | H | cyclohexyl | Cl | 114 |
| I-93 | (R)CH(CH$_3$)—CH(CH$_3$)$_2$ | H | cyclohexyl | Cl | 110 |
| I-94 | (S)CH(CH$_3$)—CH(CH$_3$)$_2$ | H | cyclohexyl | Cl | 110 |
| I-95 | (R/S)CH(CH$_3$)—C(CH$_3$)$_3$ | H | cyclohexyl | Cl | 134 |
| I-96 | (R)CH(CH$_3$)—C(CH$_3$)$_3$ | H | cyclohexyl | Cl | 116 |
| I-97 | (S)CH(CH$_3$)—C(CH$_3$)$_3$ | H | cyclohexyl | Cl | 116 |
| I-98 | (R/S)CH(CH$_3$)—CF$_3$ | H | cyclohexyl | Cl | 160 |
| I-99 | (R)CH(CH$_3$)—CF$_3$ | H | cyclohexyl | Cl | 130 |
| I-100 | (S)CH(CH$_3$)—CF$_3$ | H | cyclohexyl | Cl | 130 |
| I-101 | CH$_2$—CF$_3$ | H | cyclohexyl | Cl | 167 |
| I-102 | —(CH$_2$)$_2$CH(CH$_3$)(CH$_2$)$_2$— | | CH$_2$—C$_6$H$_5$ | Cl | 144 |
| I-103 | CH$_2$—C(CH$_3$)=CH$_2$ | CH$_2$—CH$_3$ | CH$_2$-(2-Cl—C$_6$H$_4$) | Cl | 114 |
| I-104 | —(CH$_2$)$_2$CH(CH$_3$)(CH$_2$)$_2$— | | CH$_2$-(2-Cl—C$_6$H$_4$) | Cl | 164 |
| I-105 | CH$_2$—C(CH$_3$)=CH$_2$ | CH$_2$—CH$_3$ | CH$_2$—CH=CH$_2$ | Cl | 55 |
| I-106 | —(CH$_2$)$_2$CH(CH$_3$)(CH$_2$)$_2$— | | CH$_2$—CH=CH$_2$ | Cl | 37 |
| I-107 | cyclopentyl | H | CH$_2$—CH=CH$_2$ | Cl | 43 |
| I-108 | (R/S)CH(CH$_3$)—CF$_3$ | H | cyclopropylmethyl | Cl | 150 |
| I-109 | CH$_2$—CF$_3$ | H | cyclopropylmethyl | Cl | 144 |
| I-110 | CH(CH$_3$)$_2$ | H | CH$_2$—CH$_2$—CN | Cl | 211 |
| I-111 | CH$_2$—C(CH$_3$)=CH$_2$ | CH$_2$—CH$_3$ | CH$_2$—CF$_3$ | Cl | 84 |
| I-112 | CH(CH$_3$)$_2$ | H | CH$_2$—CF$_3$ | Cl | 151 |
| I-113 | cyclopentyl | H | CH$_2$—CF$_3$ | Cl | 163 |
| I-114 | CH$_2$—CH$_3$ | CH$_2$—CH$_3$ | CH$_2$—CF$_3$ | Cl | 103 |
| I-115 | (CH$_2$)$_2$—CH$_3$ | (CH$_2$)$_2$—CH$_3$ | CH$_2$—CF$_3$ | Cl | 107 |
| I-116 | CH—(CH$_3$)$_2$ | CH$_3$ | CH$_2$—CF$_3$ | Cl | 88 |
| I-117 | (R/S)CH(CH$_3$)—CH$_2$—CH$_3$ | H | CH$_2$—CF$_3$ | Cl | 131 |
| I-118 | (R)CH(CH$_3$)—CH$_2$—CH$_3$ | H | CH$_2$—CF$_3$ | Cl | 126 |
| I-119 | (S)CH(CH$_3$)—CH$_2$—CH$_3$ | H | CH$_2$—CF$_3$ | Cl | 126 |
| I-120 | (R/S)CH(CH$_3$)—CH(CH$_3$)$_2$ | H | CH$_2$—CF$_3$ | Cl | 114 |
| I-121 | (R)CH(CH$_3$)—CH(CH$_3$)$_2$ | H | CH$_2$—CF$_3$ | Cl | 112 |
| I-122 | (S)CH(CH$_3$)—CH(CH$_3$)$_2$ | H | CH$_2$—CF$_3$ | Cl | 112 |
| I-123 | (R/S)CH(CH$_3$)—C(CH$_3$)$_3$ | H | CH$_2$—CF$_3$ | Cl | 110 |
| I-124 | (R)CH(CH$_3$)—C(CH$_3$)$_3$ | H | CH$_2$—CF$_3$ | Cl | 105 |
| I-125 | (S)CH(CH$_3$)—C(CH$_3$)$_3$ | H | CH$_2$—CF$_3$ | Cl | 105 |
| I-126 | (R/S)CH(CH$_3$)—CF$_3$ | H | CH$_2$—CF$_3$ | Cl | 179 |
| I-127 | (R)CH(CH$_3$)—CF$_3$ | H | CH$_2$—CF$_3$ | Cl | 125 |
| I-128 | (S)CH(CH$_3$)—CF$_3$ | H | CH$_2$—CF$_3$ | Cl | 125 |
| I-129 | H | H | CH$_2$—CF$_3$ | Cl | 243 |
| I-130 | CH(CH$_3$)$_2$ | H | (CH$_2$)$_7$—CH$_3$ | CF$_3$ | 91 |
| I-131 | —(CH$_2$)$_2$CH(CH$_3$)(CH$_2$)$_2$— | | (CH$_2$)$_7$—CH$_3$ | CF$_3$ | 64 |
| I-132 | cyclopentyl | H | (CH$_2$)$_7$—CH$_3$ | CF$_3$ | 84 |
| I-133 | H | H | (CH$_2$)$_7$—CH$_3$ | CF$_3$ | 177 |
| I-134 | CH(CH$_3$)$_2$ | H | (CH$_2$)$_2$—CH$_3$ | CF$_3$ | 162 |
| I-135 | —(CH$_2$)$_2$CH(CH$_3$)(CH$_2$)$_2$— | | (CH$_2$)$_2$—CH$_3$ | CF$_3$ | 108 |
| I-136 | (R)CH(CH$_3$)—C(CH$_3$)$_3$ | H | (CH$_2$)$_2$—CH$_3$ | CF$_3$ | 101 |
| I-137 | (S)CH(CH$_3$)—C(CH$_3$)$_3$ | H | (CH$_2$)$_2$—CH$_3$ | CF$_3$ | 101 |
| I-138 | H | H | (CH$_2$)$_2$—CH$_3$ | CF$_3$ | 241 |
| I-139 | CH(CH$_3$)$_2$ | H | (CH$_2$)$_7$—CH$_3$ | C$_6$H$_5$ | 83 |
| I-140 | —(CH$_2$)$_2$CH(CH$_3$)(CH$_2$)$_2$— | | (CH$_2$)$_7$—CH$_3$ | C$_6$H$_5$ | 63 |
| I-141 | H | H | (CH$_2$)$_7$—CH$_3$ | C$_6$H$_5$ | 163 |
| I-142 | —(CH$_2$)$_2$CH(CH$_3$)(CH$_2$)$_2$— | | cyclopentyl | Cl | 2960, 1610, 1550, 1241 |
| I-143 | cyclopentyl | H | cyclopentyl | Cl | 154 |
| I-144 | CH—(CH$_3$)$_2$ | CH$_3$ | cyclopentyl | Cl | 2958, 1610, 1548, 1239 |
| I-145 | (R/S)CH(CH$_3$)—CH$_2$—CH$_3$ | H | cyclopentyl | Cl | 143 |

TABLE 1-continued

| No. | R¹ | R² | R³ | X | phys. data (m.p. [° C.]; IR[cm⁻¹]; ¹H-NMR δ [ppm] |
|---|---|---|---|---|---|
| I-146 | (S)CH(CH$_3$)—CH$_2$—CH$_3$ | H | cyclopentyl | Cl | 137 |
| I-147 | (R)CH(CH$_3$)—CH$_2$—CH$_3$ | H | cyclopentyl | Cl | 137 |
| I-148 | (R/S)CH(CH$_3$)—CH(CH$_3$)$_2$ | H | cyclopentyl | Cl | 124 |
| I-149 | (S)CH(CH$_3$)—CH(CH$_3$)$_2$ | H | cyclopentyl | Cl | 110 |
| I-150 | (R)CH(CH$_3$)—CH(CH$_3$)$_2$ | H | cyclopentyl | Cl | 110 |
| I-151 | (R/S)CH(CH$_3$)—C(CH$_3$)$_3$ | H | Cyclopentyl | Cl | 113 |
| I-152 | (S)CH(CH$_3$)—C(CH$_3$)$_3$ | H | cyclopentyl | Cl | 2962, 1610, 1550, 1241 |
| I-153 | (R)CH(CH$_3$)—C(CH$_3$)$_3$ | H | cyclopentyl | Cl | 2960, 1610, 1549, 1241 |
| I-154 | (R/S)CH(CH$_3$)—CF$_3$ | H | cyclopentyl | Cl | 129 |
| I-155 | (S)CH(CH$_3$)—CF$_3$ | H | cyclopentyl | Cl | 135 |
| I-156 | (R)CH(CH$_3$)—CF$_3$ | H | cyclopentyl | Cl | 135 |
| I-157 | H | H | CH(CH$_3$)—(CH$_2$)$_5$—CH$_3$ | CF$_3$ | 129 |
| I-158 | H | H | (CH$_2$)$_3$—CH(CH$_3$)$_2$ | CF$_3$ | 213 |
| I-159 | H | H | (CH$_2$)$_6$—CH$_3$ | CF$_3$ | 180 |
| I-160 | H | H | (CH$_2$)$_5$—CH$_3$ | CF$_3$ | 208 |
| I-161 | H | H | CH(CH$_2$CH$_3$)—(CH$_2$)$_3$—CH$_3$ | CF$_3$ | 162 |
| I-162 | H | H | CH(CH$_2$CH$_2$CH$_3$)$_2$ | CF$_3$ | 164 |
| I-163 | H | H | CH(CH$_3$)—(CH$_2$)$_3$—CH$_3$ | CF$_3$ | 148 |
| I-164 | H | H | (CH$_2$)$_7$—CH$_3$ | Cl | 277 |
| I-165 | H | H | cyclopentyl | Cl | 8.4(s); 8.2(m); 3.45(m); 1.95(m); 1.8(m); 1.6(m) |
| I-166 | H | H | cyclohexyl | Cl | 8.45(s); 8.2(m); 3.1(m); 2.1(m); 1.8(m); 1.55(m); 1.4(m) |
| I-167 | CH$_2$—CH$_3$ | CH$_2$—CH$_3$ | (CH$_2$)$_7$—CH$_3$ | CN | see example 10 |
| I-168 | CH$_2$—CH$_3$ | CH$_2$—CH$_3$ | (CH$_2$)$_7$—CH$_3$ | OCH$_3$ | see example 11 |

Examples of the Action Against Harmful Fungi

The fungicidal action of the compounds of the formula I was demonstrated by the following tests:

The active compounds were prepared separately or jointly as a 10% strength emulsion in a mixture of 70% by weight of cyclohexanone, 20% by weight of Necanil® LN (Lutensol® AP6, wetting agent having emulsifying and dispersing action based on ethoxylated alkylphenols) and 10% by weight of Wettol® EM (nonionic emulsifyier based on ethoxylated castor oil) and diluted with water to the desired concentration.

Use Example 1

Activity Against *Botrytis cinerea* on Bell Pepper Leaves

Bell pepper seedlings of the cultivar "Neusiedler Ideal Elite" were, after 4-5 leaves were well-developed, sprayed to runoff point with an aqueous preparation of active compound which had been prepared from a stock solution of 10% of active compound, 85% of cyclohexanone and 5% of emulsifier. The next day, the treated plants were inoculated with a spore suspension of *Botrytis cinerea* which contained 1.7×10⁶ spores/ml in a 2% strength aqueous biomalt solution. The test plants were then placed in a climatized chamber at 22-24° C. and high atmospheric humidity. After 5 days, the extent of the fungal attack on the leaves could be determined visually in %.

In this test, the plants treated with 250 ppm of active compounds I-10, I-61, I-65, I-66, I-68, I-69, I-76, I-78, I-84, I-100, I-101, I-146 and I-153 to I-155 showed no or at most 15% infection, whereas the untreated plants were 90% infected.

Use Example 2

Activity Against Downy Mildew on Grapevines (*Plasmopara viticola*)

Leaves of potted vines of the cultivar "Müller-Thurgau" were sprayed to runoff point with an aqueous preparation of active compound which had been prepared from a stock solution of 10% of active compound, 85% of cyclohexanone and 5% of emulsifier. The next day, the leaves were inoculated with an aqueous zoospore suspension of *Plasmopara viticola*. The grapevines were initially placed in a water-vapor-saturated chamber at 24° C. for 48 hours and then in a greenhouse at 20-30° C. for 5 days. After this period of time, the plants were once more placed into a moist chamber for 16 hours to promote sporangiophore eruption. The extent of the development of the infection on the undersides of the leaves was then determined visually.

In this test, the plants treated with 250 ppm of active compounds I-8, I-10, I-19, I-25, I-27, I-49, I-60 to I-62, I-69, I-84, I-101, I-113, I-133, I-146 and I-153 to I-155 showed no or at most 15% infection, whereas the untreated plants were 85% infected.

We claim:

1. A 7-aminotriazolopyrimidine compound of the formula I,

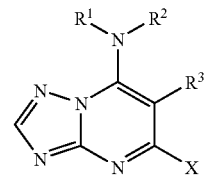

where:
R¹, R² are hydrogen, $C_1$-$C_{10}$-alkyl, $C_2$-$C_{10}$-alkenyl, $C_2$-$C_{10}$-alkynyl, $C_3$-$C_8$-cycloalkyl, phenyl, naphthyl; or
5- or 6-membered heterocyclyl containing one to four nitrogen atoms or one to three nitrogen atoms and one sulfur or oxygen atom; or
5- to 6-membered heteroaryl containing one to four nitrogen atoms or one to three nitrogen atoms and one sulfur or oxygen atom,
where R¹ and R², independently of one another, may, if they are not hydrogen, be partially or fully halogenated and/or may carry one to three radicals from the group $R^a$
$R^a$ is cyano, nitro, hydroxyl, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-al-kylthio, $C_1$-$C_6$-alkylamino, di-$C_1$-$C_6$-alkylamino, $C_2$-$C_6$-al-kenyl, $C_2$-$C_6$-alkenyloxy, $C_2$-$C_6$-alkynyl, $C_3$-$C_6$-alkynyloxy and unhalogenated or halogenated oxy-$C_1$-$C_4$-alkyleneoxy; or
R¹ and R² together with the linking nitrogen atom may form a 5- to 6-membered ring which contains one to four nitrogen atoms or one to three nitrogen atoms and one sulfur or oxygen atom and whcih may be substituted by one to three radicals from the group $R^a$;
R³ is $C_1$-$C_{10}$-alkyl, $C_2$-$C_{10}$-alkenyl, $C_2$-$C_{10}$-alkynyl-, $C_3$-$C_8$-cy-cloalkyl, phenyl-$C_1$-$C_{10}$-alkyl,
where R³ may be unsubstituted or partially or fully halogenated and/or may carry one to three radicals from the group $R^a$, or
$C_1$-$C_{10}$-haloalkyl which may carry one to three radicals from the group $R^a$;
X is halogen, cyano, $C_1$-$C_4$-alkoxy, $C_1$-$C_4$-haloalkyl, phenyl or $R^a$-substituted phenyl;
salts thereof.

2. A 7-aminotriazolopyrimidine compound of the formula I as claimed in claim 1 in which X is halogen.

3. A 7-aminotriazolopyrimidine compound selected from the group consisting of:
(5-chloro-6-ethyl-[1,2,4]triazolo[1,5-a]pyrimidin-7-yl)-cyclopentyl-amine;
(5-chloro-6-ethyl-[1,2,4]triazolo[1,5-a]pyrimidin-7-yl)-(S)-(1,2-dimethyl-propyl)-amine;
(5-chloro-6-ethyl-[1,2,4]triazolo[1,5-a]pyrimidin-7-yl)-(S)-(2,2,2-trifluor-1-methyl-ethyl) -amine;
6-butyl-5-chloro-7-(4-methyl-piperidin-1-yl)-(1,2,4,]triazolo[1,5-a]pyrimidine;
(5-chloro-6-octyl-[1,2,4]triazolo[1,5-a]pyrimidin-7-yl)-dipropylamine;
(5-chloro-6-isopropyl-[1,2,4]triazolo[1,5-a]pyrimidin-7-yl)-ethyl-(2-methyl-allyl)-amine;
(5-chloro-6-isopropyl-[1,2,4]triazolo[1,5-a]pyrimidin-7-yl)-isopropyl-amine;
(5-chloro-6-isopropyl-[1,2,4]triazolo[1,5-a]pyrimidin-7-yl)-diethyl-amine;
(R/S)-sec-butyl-(5-chloro-6-isopropyl-[1,2,4]triazolo[1,5-a]pyrimidin-7-yl)-amine;
(R)-sec-butyl-(5-chloro-6-isopropyl-[1,2,4]triazolo[1,5a]pyrimidin-7-yl)-amine;
(5-chloro-6-isopropyl-[1,2,4]triazolo[1,5a]pyrimidin-7-yl)-(R/S)-(1,2-dimethyl-propyl)-amine;
(5-chloro-6-isopropyl-[1,2,4]triazolo[1,5-a]pyrimidin-7-yl)-(R)-(1,2-dimethyl-propyl)-amine;
(5-chloro-6-isopropyl-[1,2,4]triazolo[1,5-a]pyrimidin-7-yl)-(S)-(2,2,2-trifluoro-1-methylethyl)-amine;
(5-chloro-6-cyclopentyl-[1,2,4]triazolo[1,5-a]pyrimidin-7-yl)-ethyl-(2-methyl-allyl)-amine;
(5-chloro-6-cyclohexyl-[1,2,4]triazolo[1,5-a]pyrimidin-7-yl)-(S)-(2,2,2-trifluoro-1-methylethyl)-amine;
(5-chloro-6-cyclohexyl-[1,2,4]triazolo[1,5-a]pyrimidin7-yl)-ethyl-amine;
[5-chloro-6-(2,2,2-trifluoro-ethyl)-[1,2,4]triazolo[1,5-a]pyrimidin-7-yl]-cyclopentyl-amine;
6-octyl-5-trifluoromethyl-[1,2,4]triazolo[1,5-a]pyrimidin-7-ylamine;
sec-butyl-(5-chloro-6-cyclopentyl-[1,2,4]triazolo[1,5-a]pyrimidin-7-yl)-amine;
(5-chloro-6-cyclopentyl-[1,2,4]triazolo[1,5-a]pyramidin-7-yl)-(R)-(1,2,2-trimethyl-propyl)-amine;
(5-chloro-6-cyclopentyl-[1,2,4]triazolo[1,5-a]pyrimidin-7-yl)-(R/S)-(2,2,2-trifluoro-1-methylethyl)-amine; and
(5-chloro-6-cyclopentyl-[1,2,4]triazolo[1,5-a]pyrimidin-7-yl)-(S)-(2,2,2-trifluoro-1-methylethyl)-amine.

4. A 7-aminotriazolopyrimidine compound selected from the group consisting of:
(5-chloro-6-isobutyl-[1,2,4]triazolo[1,5-a]pyrimidin-7-yl)-(2-methyl-allyl)-amine;
(5-chloro-6-isobutyl-[1,2,4]triazolo[1,5-a]pyrimidin-7-yl)-isopropyl-amine;
sec-butyl-(5-chloro-6-isobutyl-[1,2,4]triazolo[1,5-a]pyrimidin-7-yl)-amine;
(5-chloro-6-isopropyl-[1,2,4]triazolo[1,5-a]pyrimidin-7-yl)-isopropyl-amine;
5-chloro-6-cyclohexyl-7-(4-methyl-piperidin-1-yl)-[1,2,4]triazolo[1,5-a]pyrimidine;
(5-chloro-6-cyclopentyl-[1,2,4]triazolo[1,5-a]pyrimidin-7-yl)-cyclopentyl-amine; and
(5-chloro-6-cyclopentyl-[1,2,4]triazolo[1,5-a]pyrimidin-7-yl)-(R/S)-(1,2,2-trimethyl-propyl)-amine.

5. A 7-aminotriazolopyrimidine compound selected from the group consisting of:
6-isobutyl-5-trifluoromethyl-[1,2,4]triazolo[1,5a]pyrimidin-7-ylamine;
6-(1-methyl-butyl)-5-trifluoromethyl-[1,2,4]triazolo[1,5-a]pyrimidin-7-ylamine;
6-tert-butyl-5-trifluoromethyl-[1,2,4]triazolo[1,5-a]pyrimidin-7-ylamine;
6-isopropyl-5-trifluoromethyl-[1,2,4]triazolo[1,5-a]pyrimidin-7-ylamine;
6-cyclopentyl-5-trifluoromethyl-[1,2,4]triazolo[1,5-a]pyrimidin-7-ylamine;
6-cyclohexyl5-trifluoromethyl-[1,2,4]triazolo[1,5-a]pyrimidin-7-ylamine;
6-benzyl-5-trifluoromethyl-[1,2,4]triazolo[1,5-a]pyrimidin-7-yl-amine;
6-(4-chloro-benzyl)-5-trifluoromethyl-[1,2,4]triazolo[1,5-a]pyrimidin-7-ylamine;
5-chloro-6-ethyl-[1,2,4]triazolo[1,5-a]pyrimidin-7-ylamine;
5-chloro-6-isopropyl-[1,2,4]triazolo[1,5-a]pyrimidin-7-ylamine;
5-chloro-6-(2,2,2-trifluoroethyl)-[1,2,4]triazolo[1,5-a]pyrimidin-7-ylamine;
6-propyl-5-trifluoromethyl-[1,2,4]triazolo[1,5-a]pyrimidin-7-yl-amine;
6-(1-methyl-heptyl)-5-trifluoromethyl-[1,2,4]triazolo[1,5-a]pyrimidin-7-ylamine;
6-(4-methyl-pentyl)-5-trifluoromethyl-[1,2,4]triazolo[1,5-a]pyrimidin-7-ylamine;

6-heptyl-5-trifluoromethyl-[1,2,4]triazolo[1,5-a]pyrimidin-7-yl-amine;
6-hexyl-5-trifluoromethyl-[1,2,4]triazolo[1,5-a]pyrimidin-7-yl-amine;
6-(1-ethyl-pentyl)-5-trifluoromethyl-[1,2,4]triazolo[1,5-a]pyrimidin-7-ylamine;
6-(1-propyl-butyl)-5-trifluoromethyl-[1,2,4]triazolo[1,5-a]pyrimidin-7-ylamine;
6-(1-methyl-pentyl)-5-trifluoromethyl-[1,2,4]triazolo[1,5-a]pyrimidin-7-ylamine;
5-chloro-6-octyl-[1,2,4]triazolo[1,5-a]pyrimidin-7-ylamine;
5-chloro-6-cyclopentyl-[1,2,4]triazolo[1,5-a]pyrimidin-7-ylamine; and
5-chloro-6-cyclohexyl-[1,2,4]triazolo[1,5-a]pyrimidin-7-ylamine.

6. A process for preparing the 7-aminotriazolopyrimidine compound of the formula I as claimed in claim 1, in which X is halogen, cyano or $C_1$-$C_4$alkoxy, which comprises cyclizing dicarbonyl compounds of the formula II.1,

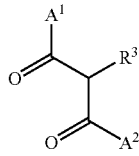

where $A^1$ and $A^2$ are $C_1$-$C_{10}$-alkoxy, with 3-amino-1,2,4-triazole of the formula III

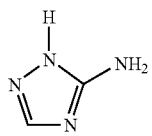

to give hydroxytriazolopyrimidines of the formula IV.1

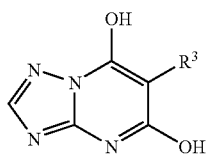

halogenating the hydroxytriazolopyrimidines of the formula IV.1 with a halogenating agent to give halotriazolopyrimidines of the formula V.1

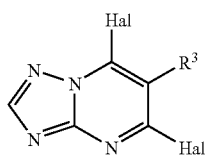

where Hal is halogen, followed by reaction with an amine of the formula VI

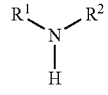

to give 7-aminotriazolopyrimidines of the formula I in which X is halogen, and, to prepare 7-aminotriazolopyrimidines of the formula I in which X is cyano or $C_1$-$C_4$-alkoxy, reacting with a compound of the formula VII

M-X'      VII in which M is an ammonium, tetraalkylammonium, alkali metal or alkaline metal cation and X' is cyano or alkoxy.

7. A process for preparing compounds of the formula I as claimed in claim 1, in which X is $C_1$-$C_4$-haloalkyl or unsubstituted or $R^a$-substituted phenyl, which comprises cyclizing dicarbonyl compounds of the formula II.2

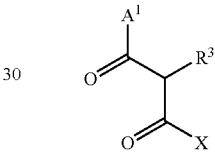

where $A^1$ is $C_1$-$C_{10}$-alkoxy and X is $C_1$-$C_4$-haloalkyl or unsubstituted or $R^a$-substituted phenyl with 3-amino-1,2,4-triazole of the formula III as claimed in claim 3 to give 7-hydroxytriazolopyrimidines of the formula IV.2

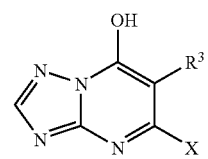

halogenating the 7-hydroxytriazolopyrimidines of the formula IV.2 with a halogenating agent to give 7-halotriazolopyrimidines of the formula V.2

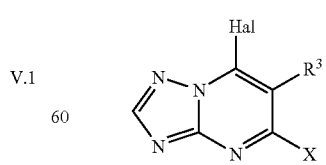

where Hal is halogen, followed by reaction with an amine of the formula VI as claimed in claim 3 to give 7-aminotriazolopyrimidines of the formula I.

8. A method for controlling harmful fungi, which comprises treating the fungi or the materials, plants, the soil or the seeds to be protected against fungal attack with an effective amount of the 7-aminotriazolopyrimidine compound of the formula I as claimed in claim 1.

9. A composition suitable for controlling harmful fungi, which comprises a solid or liquid carrier and a 7-aminotriazolopyrimidine compound of the formula I as claimed in claim 1.

10. A method for preparing the composition as claimed in claim 9 which comprises combining the 7-aminotriazolopyrimidine of the formula I and the solid or liquid carrier.

* * * * *

UNITED STATES PATENT AND TRADEMARK OFFICE
CERTIFICATE OF CORRECTION

PATENT NO. : 7,307,172 B2
APPLICATION NO. : 10/484250
DATED : December 11, 2007
INVENTOR(S) : Tormo i Blasco et al.

It is certified that error appears in the above-identified patent and that said Letters Patent is hereby corrected as shown below:

Title Page, Item (12)
"Blasco et al." should read --Tormo i Blasco et al.--
Claim 1, Col. 35, line 16: "$C_1$-$C_6$-al-kylthio" should read --$C_1$-$C_6$-alkylthio--
Claim 1, Col. 35, line 17: "$C_2$-$C_6$-al-kenyl" should read --$C_2$-$C_6$-alkenyl--
Claim 1, Col. 35, line 24: "whcih" should read --which--
Claim 1, Col. 35, line 27: "$C_3$-$C_8$-cy-cloalkyl" should read --$C_3$-$C_8$-cycloalkyl--
Claim 1, Col. 35, line 35: "salts thereof" should read --or salts thereof--
Claim 3, Col. 35, line 58: "[1, 5a]" should read --[1, 5-a]--
Claim 3, Col. 35, line 60: "[1, 5a]" should read --[1, 5-a]--
Claim 5, Col. 36, line 48: "6-cyclohexyl5-trifluoromethyl" should read
--6-cyclohexyl-5-trifluoromethyl--
Claim 6, Col. 37, line 19: "$C_1$-$C_4$alkoxy" should read --$C_1$-$C_4$-alkoxy--
Claim 10, Col. 40, line 5: "of the formula" should read --compound of the formula--

Signed and Sealed this

Twenty Second Day of April, 2008

JON W. DUDAS
*Director of the United States Patent and Trademark Office*